US010595857B2

(12) United States Patent
Heneveld

(10) Patent No.: US 10,595,857 B2
(45) Date of Patent: *Mar. 24, 2020

(54) NEEDLE AND GUIDE APPARATUS FOR PASSING SUTURE

(71) Applicant: SUTURE EASE, INC., San Jose, CA (US)

(72) Inventor: Scott Heneveld, Whitmore, CA (US)

(73) Assignee: SUTURE EASE, INC., San Jose, CA (US)

( * ) Notice: Subject to any disclaimer, the term of this patent is extended or adjusted under 35 U.S.C. 154(b) by 295 days.

This patent is subject to a terminal disclaimer.

(21) Appl. No.: 15/485,075

(22) Filed: Apr. 11, 2017

(65) Prior Publication Data

US 2017/0238922 A1    Aug. 24, 2017

Related U.S. Application Data

(63) Continuation-in-part of application No. 14/800,532, filed on Jul. 15, 2015, now Pat. No. 9,668,727, which
(Continued)

(51) Int. Cl.
*A61B 17/04* (2006.01)
*A61B 17/06* (2006.01)
*A61B 17/00* (2006.01)

(52) U.S. Cl.
CPC ...... *A61B 17/0482* (2013.01); *A61B 17/0057* (2013.01); *A61B 17/0469* (2013.01);
(Continued)

(58) Field of Classification Search
CPC ............ A61B 17/0469; A61B 17/0482; A61B 17/0483; A61B 17/0485
See application file for complete search history.

(56) References Cited

U.S. PATENT DOCUMENTS 9,668,727 B2 *  6/2017  Heneveld ........... A61B 17/0057
2009/0018554 A1 *  1/2009  Thorne .............. A61B 17/0485
606/145

(Continued)

OTHER PUBLICATIONS

Communication pursuant to Article 94(3) EPC dated Sep. 22, 2017 from corresponding European Application No. 13761889.8.
(Continued)

*Primary Examiner* — Sarah A Simpson
(74) *Attorney, Agent, or Firm* — Innovation Capital Law Group, LLP; Vic Lin

(57) ABSTRACT

A trocar wound closure system includes a suture passing needle and a guide for directing the needle through the wound site. A distal portion of the needle includes a capture rod with a slot. An obturator tube with a cutout section can be axially actuated to align the cutout section with the slot, and then moved out of alignment so as to capture the suture. The guide includes at least two tracks for directing the needle through the tissue track. A suture catcher is located adjacent to the exit of each track, and configured to be actuated from a radially extended configuration to a retracted configuration so as to capture the suture section inserted through each loop. Radially expandable arms at distal section are movable between an expanded configuration and a slender configuration.

21 Claims, 30 Drawing Sheets

Related U.S. Application Data is a continuation-in-part of application No. 13/787,243, filed on Mar. 6, 2013, now Pat. No. 9,393,011.

(60) Provisional application No. 62/024,700, filed on Jul. 15, 2014, provisional application No. 61/723,262, filed on Nov. 6, 2012, provisional application No. 61/610,354, filed on Mar. 13, 2012.

(52) U.S. Cl.
CPC .... *A61B 17/06066* (2013.01); *A61B 17/0485* (2013.01); *A61B 2017/00637* (2013.01); *A61B 2017/00663* (2013.01); *A61B 2017/0472* (2013.01); *A61B 2017/0496* (2013.01); *A61B 2017/061* (2013.01); *A61B 2017/06042* (2013.01)

(56) References Cited

U.S. PATENT DOCUMENTS

2011/0245850 A1   10/2011  Burg et al.
2012/0035623 A1*  2/2012  Bagaoisan ......... A61B 17/0057
                                                     606/144

OTHER PUBLICATIONS

Final Office Action dated Jan. 25, 2018 from corresponding U.S. Appl. No. 15/096,610.

\* cited by examiner

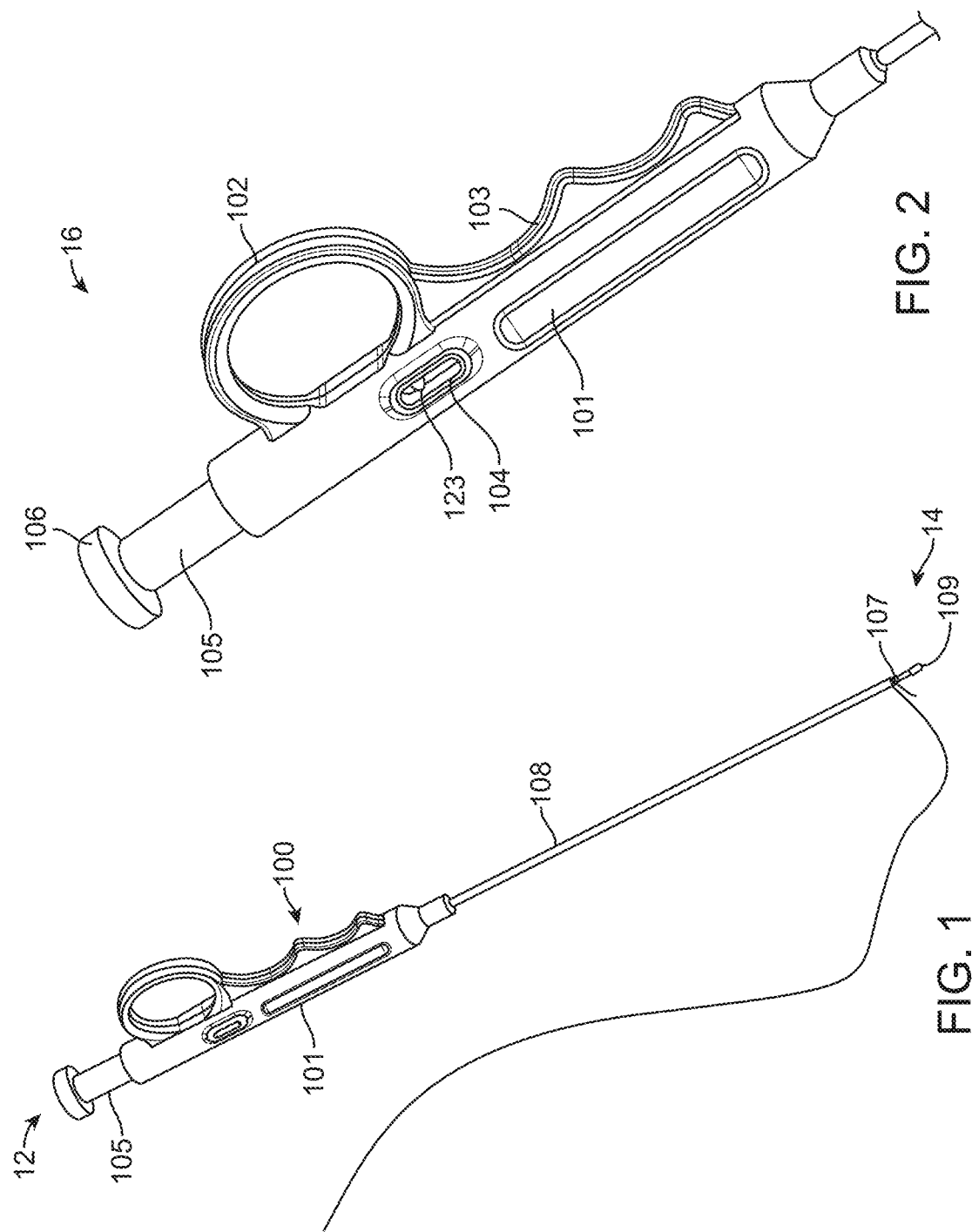

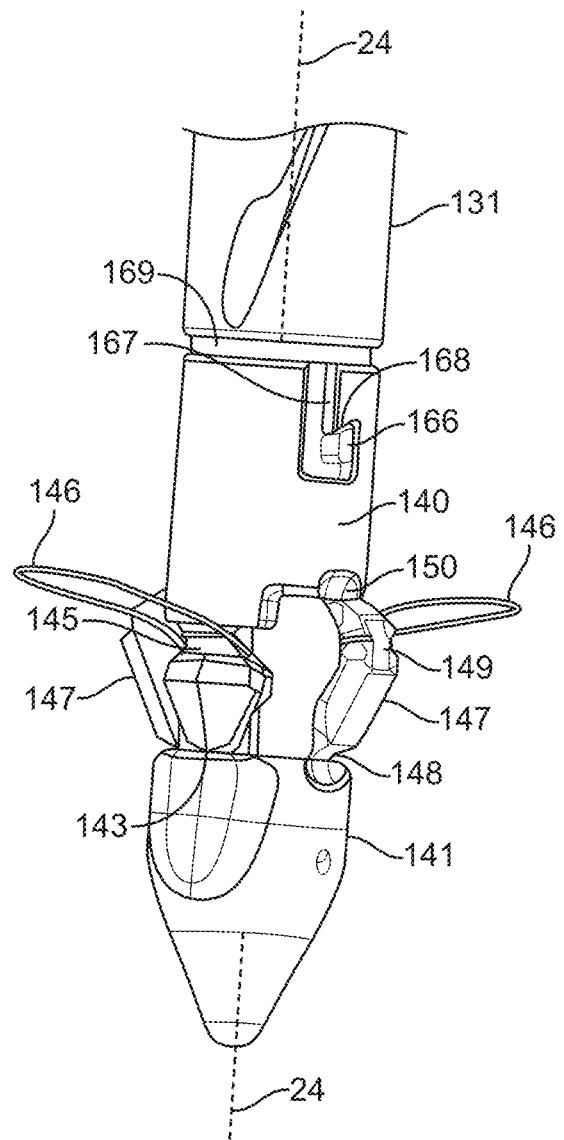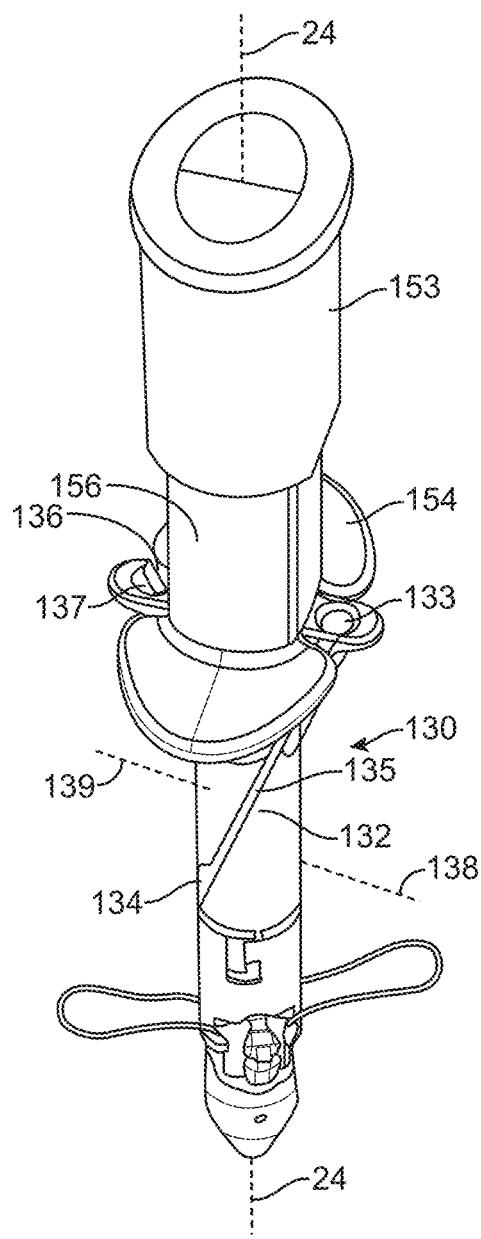
FIG. 7
FIG. 8

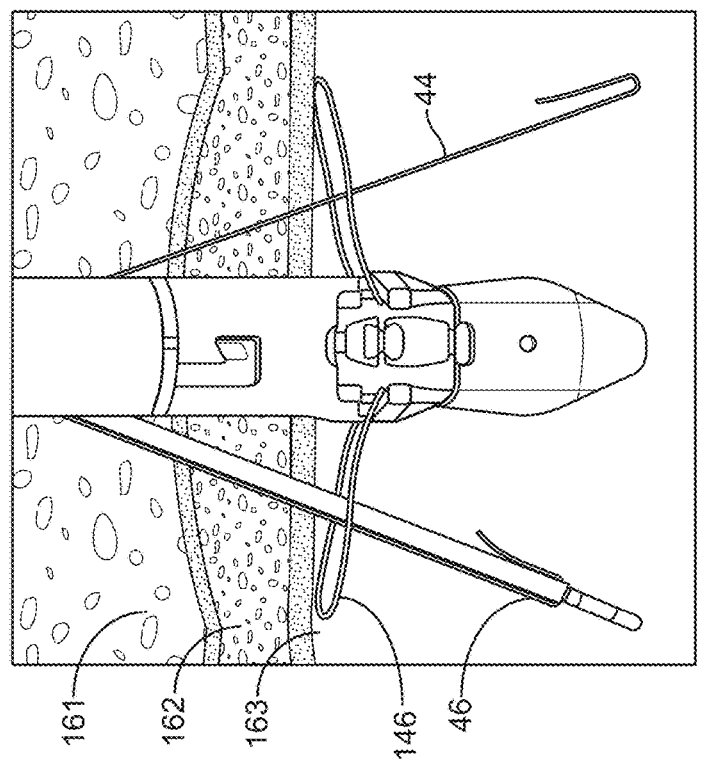
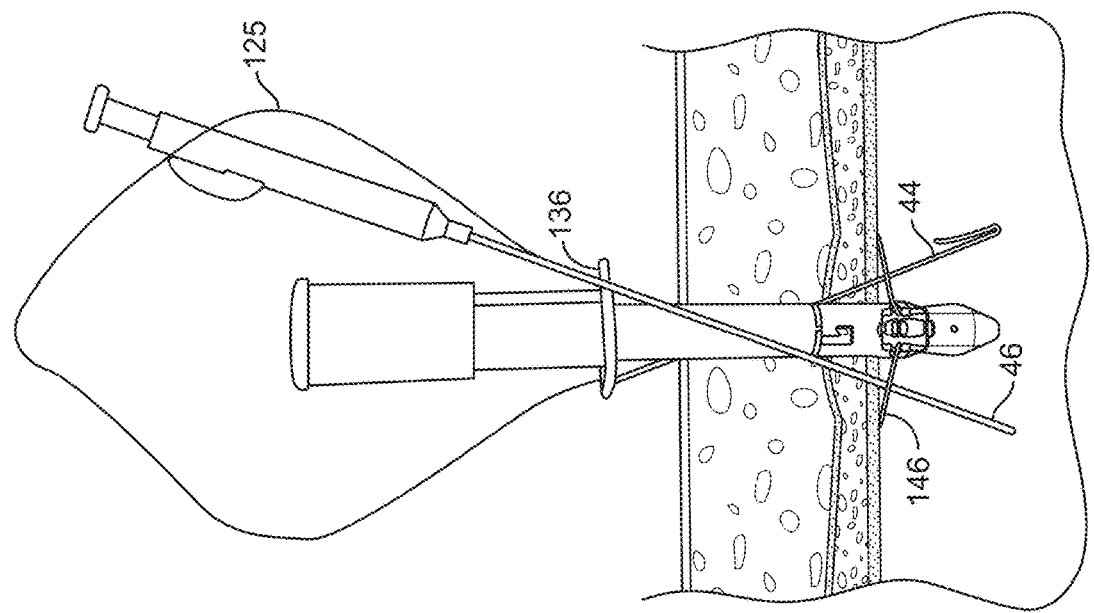
FIG. 13B
FIG. 13A

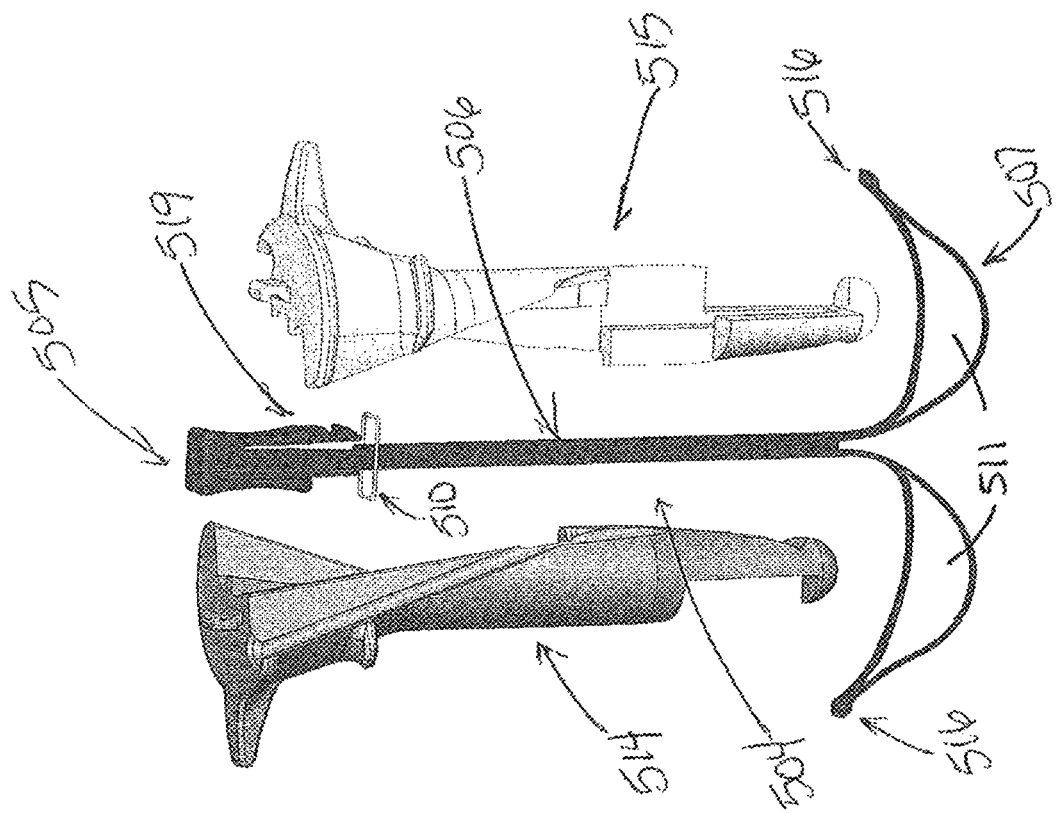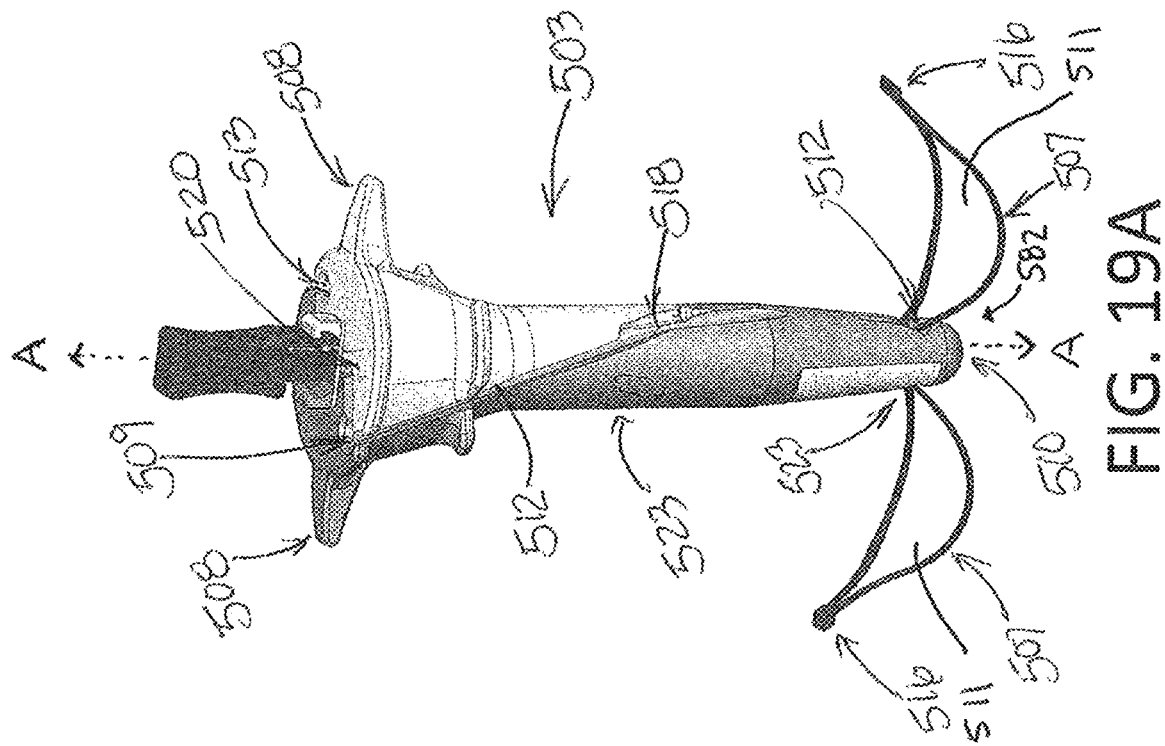

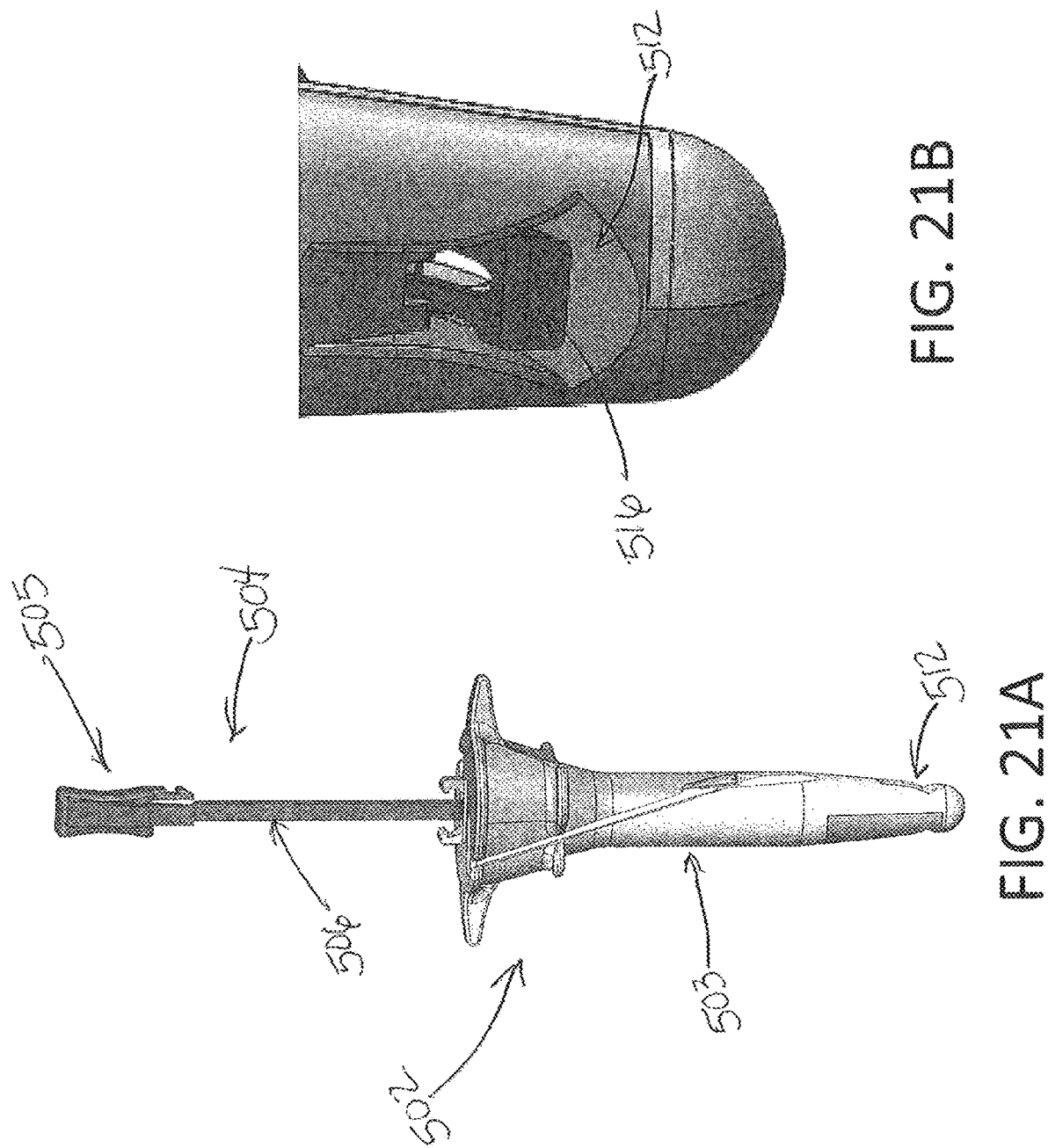

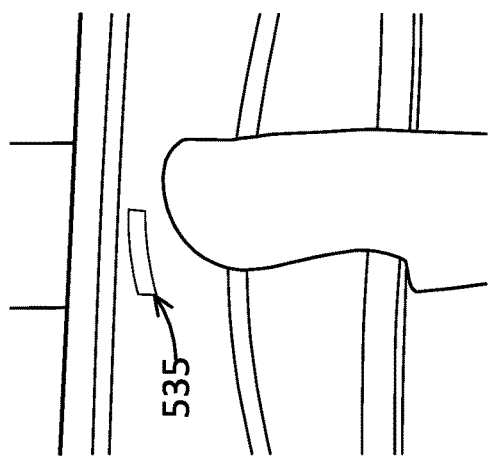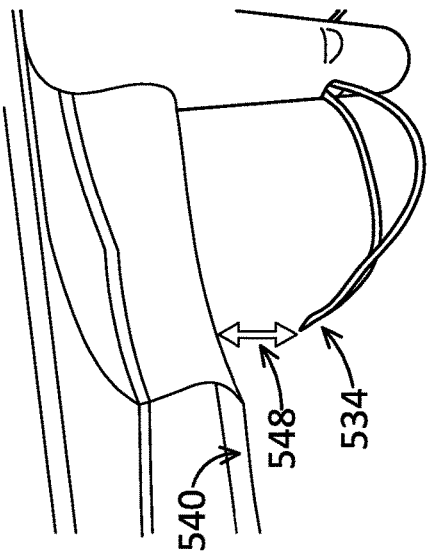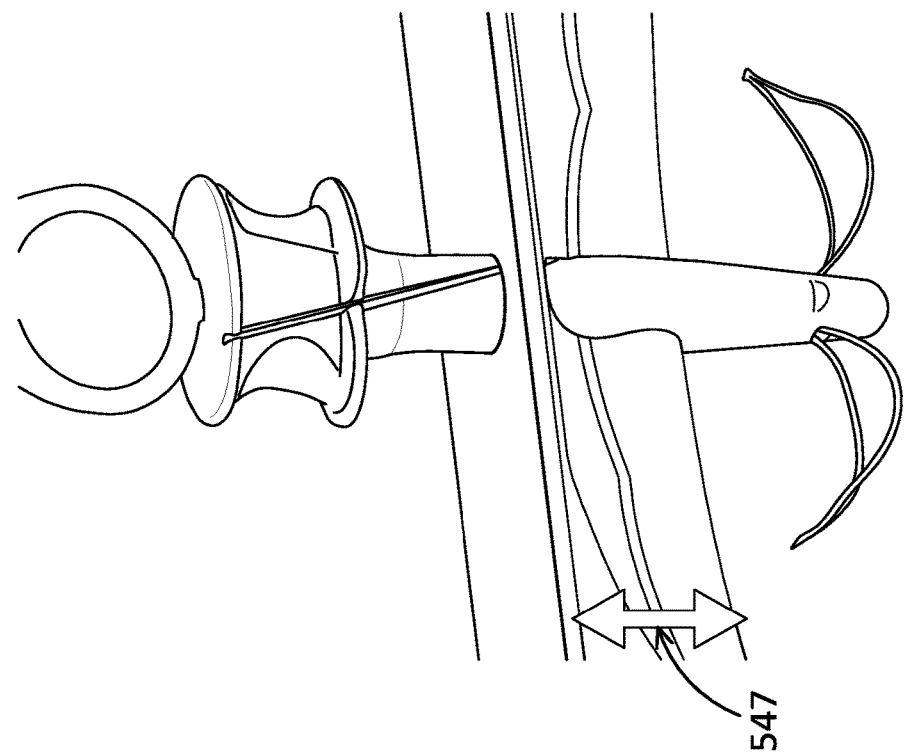

NEEDLE AND GUIDE APPARATUS FOR PASSING SUTURE

RELATED APPLICATIONS

This application is a continuation-in-part of U.S. Non-Provisional patent application Ser. No. 14/800,532 filed on Jul. 15, 2015 which is a continuation-in-part of U.S. Non-Provisional patent application Ser. No. 13/787,243 filed on Mar. 6, 2013. This application also relates to, claims priority from, and incorporates herein by reference, as if fully set forth:
1) U.S. Provisional Patent Application No. 61/610,354 filed on Mar. 13, 2012 and entitled "METHOD AND SNARE GUIDE APPARATUS FOR PASSING SUTURE";
2) U.S. Provisional Patent Application No. 61/723,262 filed on Nov. 6, 2012 and entitled "METHOD AND SAFETY NEEDLE APPARATUS FOR PASSING SUTURE"; and
3) U.S. Provisional Patent Application No. 62/024,700 filed on Jul. 15, 2014 and entitled "NEEDLE AND MONOLITHIC SNARE GUIDE APPARATUS FOR CLOSING SUTURE."

BACKGROUND OF THE INVENTION

Field of the Invention

This invention relates to surgical instruments for approximation, ligation and fixation of tissue using a suture, and particularly to the approximation of tissue separated by mean of an endosurgical trocar being inserted into a body cavity.

Description of Prior Art and Related Information

Numerous methods currently exist for performing laparoscopic procedures. One of the more commonly used methods is known as closed laparoscopy which utilizes a sharp needle (e.g., Veress needle) to puncture the abdominal wall and insufflate the abdominal cavity with an inert gas such as carbon dioxide through the needle. This process of insufflating the cavity separates the abdominal wall from the underlying organs creating a gap for the surgeon to work within. A trocar/cannula system is then used to maintain the insufflated cavity and provide a working portal for which instruments can be passed into and out of the abdominal cavity to perform various surgical procedures. When the procedure is completed, it is desirable for the surgeon to close the incision site using suture material to minimize the risk of adverse post-operative events.

One of the post-operative complications associated with this procedure is the incidence of trocar site hernias, where a portion of an organ or fatty tissue protrudes out through the hole in the abdominal wall created by the trocar access portal. It is believed that improper closure, or complete lack of closure, of the incision site at the peritoneum is the primary cause of these hernias which form during the post-operative period ranging from several days to several months following the procedure. Traditional methods of wound site close require an additional set of instruments (suture passers, guides, etc.) to be introduced into the surgery. A number of these instruments have been previously disclosed. However, the prior art related to trocar wound site closure instrumentation are typically cumbersome to use and do not provide for a simple, reproducible, and reliable means of closing the wound site.

BRIEF SUMMARY OF THE INVENTION

A preferred system according to the invention comprises a surgical instrument as well as a surgical instrument set that may have certain functions. First, the system may have the capabilities to provide entry into the abdominal cavity and subsequently insufflating the cavity for use in laparoscopic surgical procedures. In the preferred embodiment, the system comprises a needle apparatus having a sharp needle tip and an insufflation channel to facilitate penetration into the abdominal cavity and insufflation. A unique obturator tip is provided to shield the sharp needle tip upon insertion into the cavity. Second, the system may have the capabilities to close the fascial/peritoneal layer at the trocar wound site in a quick, consistent and reproducible manner at the end of the procedure. To facilitate closure of the wound, the system includes the same needle used in combination with a guide apparatus which has suture capture features disposed at or near the distal tip.

The needle apparatus may also serve as a suture passer, in that it has the ability to carry and retrieve suture through tissue layers for suturing closed the wound site. The needle apparatus also has the ability to insufflate the abdomen during the laparoscopic procedure. The needle apparatus may comprise several components including: a handle, actuation mechanism, a connector for connecting the needle to a gas line, a capture rod, an outer needle shaft, and a spring loaded safety tip on a hollow obturator tube.

In a preferred embodiment, a handle at the proximal end of the needle apparatus allows for single-handed or double-handed use. The handle may also contain a finger loop or loops for additional security while holding the needle. An actuator mechanism may be disposed adjacent to the handle and configured for the deployment and retraction of the capture rod used to secure the suture material within the tip of the needle. The preferred actuator mechanism may include a sliding plunger that translates along the long axis of the handle that moves the capture rod between a first position in an axially extended configuration and a second position in an axially retracted configuration. The actuator may be spring loaded in one direction such that the capture rod is biased to the retracted position. This may allow the suture to be passively captured without actuation of the plunger. The handle and actuator means may be constructed from metals (such as stainless steel, titanium or aluminum) or plastics (such as polyacetal, nylon, polypropylene, polyether-ether-ketone, or polycarbonate), or any combination of the two.

A long outer needle shaft may be connected to the proximal handle and extends distally over a length that may range from 2-38 centimeters, or more preferably between 10-20 centimeters. The outer needle shaft may have a sharp tip, or needle peak, at the distal-most point to ease the insertion of the needle through the various tissue layers. The outer shaft may house an obturator tube that has a hollow, unobstructed inner lumen, with a blunt tip. The obturator tube may also house a capture rod used for securing the suture for passing through tissue. The outer needle shaft, obturator tube and capture rod would optimally be constructed from metals such as stainless steel, titanium or aluminum.

The distal-most end of the obturator tube may have a blunt or rounded plug or surface at the tip. The entire obturator tube may be spring loaded to allow for the blunt tip to translate away from the tip of the needle when it is loaded, and passively travel back to the tip of the needle when it is unloaded. The obturator spring may be housed within the handle. The spring loaded obturator would serve as a safety mechanism for protecting the internal organs within the abdomen after the needle is passed through the abdominal wall.

A portion of the wall of the outer needle shaft may be cutout near the distal tip which may be used to create a slot to accommodate the suture during the suture passing process. Similarly, a portion of the wall of the obturator tube may be cut out near the distal tip of the tube to provide an opening for the capture rod to secure the suture to the wall of the outer needle shaft. The window cutout in the obturator tube must be long enough such that it can accommodate the suture as it travels back and forth. Lastly, the capture rod has a slot with one or more ramped faces. A distal ramped surface on the capture rod slot is used to capture the suture against the outer needle shaft. A proximal ramped surface may assist in pushing the suture out of the window in the obturator tube, facilitating the release of the suture from the needle.

The needle capture rod is used to secure the suture to the needle for suture passing activities. Initially the actuator may be pressed to extend the capture rod and expose the slot in the capture rod. A section of suture may be placed into the slot, and the actuator is released to retract the capture rod. As the capture rod retracts, the suture becomes trapped between the distal surface of the slot in the capture rod and the cutout in the outer needle shaft. When the suture needs to be released, the actuator may be pressed again to extend the capture rod. As the capture rod is extended the proximal face of the slot may push the suture material out of the cutout in the obturator tube and away from the needle shaft.

In another preferred embodiment, a luer connector or other quick connect type device may be disposed on the proximal handle to provide an entry passageway for the gas to enter into the needle. The unobstructed inner lumen of the obturator tube may allow for the passage of an inert gas for insufflation of the abdomen.

The guide apparatus may serve dual purposes, as it first may be used to guide the needle through the abdominal wall in a repeatable manner, and second used to capture the suture material after it is passed into the abdominal wall. The guide may comprise a slotted barrel, collapsible barrel tip, plunger, main shaft, cap, suture catchers such as a capturing snare cord, and guide tubes along with various fasteners and springs.

The slotted barrel may have two slotted channels to accommodate the passage of the needle. The entries and exits of the two channels may be spaced 180 degrees radially apart from each other such that the stitch can be placed on opposing sides of the wound. The channels' purpose is to guide the needle repeatably through the same tissue thickness and into the suture snare cord, where the suture can be released. The trajectory of the channels is referenced off the inner wall of the peritoneum such that approximately 5-15 millimeters of tissue bite is achieved from the periphery of the wound. The proximal ends of the channels may have a widened and or tapered opening to ease the entry of the needle into the channels. Slots in the channels will allow for the middle section of the length of suture to be released from the constraints of the guide channels. The width of the slots in the channels should be large enough for the suture to easily be released from the channels, yet small enough to not allow the needle to exit the channel or get caught against it.

The guide may comprise a main shaft that is slidably disposed within the slotted barrel of the guide. The main shaft may be used to actuate the expanding arms, comprising living hinges in the preferred embodiment on the collapsible barrel tip. One or more expanding arms may be used to locate the guide against the inner peritoneal wall as a reference point to ensure consistent tissue bite depth of the needle, as previously described. The main shaft may be spring loaded in a proximal position such that the expanding arms are biased to a radially expanded position where the outer profile of the arms exceeds the diameter of the slotted barrel. As the main shaft moves distally, the arms may be contracted such that aligns their outer diameter with the outer diameter of the slotted barrel in a continuous slender fashion. The main shaft may be connected at the distal end to the barrel tip, and connected to the plunger on the proximal end.

The distal end of the barrel tip may have a blunt tip to minimize the potential of harm or damage to the adjacent tissues during insertion. Moving proximally away from the blunt tip, the outer wall of the barrel tip may have a tapered region that gradually radially increases to the outer profile of the guide as designated by the outer diameter of the slotted barrel. The tapered section may facilitate the ease of insertion of the guide into the trocar wound site.

The barrel tip may have one or more stop tabs that provide a hard stop for the barrel tip as the expanding arms are actuated, to prevent excessive flexion in the hinge material. Along the length of the stop tabs, a cutout section may exist for the suture catcher, such as snare loop, to be retracted into for capturing the suture material against the guide.

The guide may have a slider that is used to actuate the snare cord material. The slider may be slidably disposed on the slotted barrel. Two suture catchers, such as snare cords, may be connected at their ends to the slider body, with a loop formed at the distal tip of the guide. The slider may be spring loaded such that the snare cords are biased into a radially extended position. As the slider is pulled proximally, the snare cord is retracted against the extension arms of the barrel tip. As the slider is released distally, the snare cord is radially extended out and away from the barrel to create two snare loops for the suture to be passed into. The slider may have two tabs that can be used to pull the slider proximally using one or more fingers on each tab. The snare cords may be constructed from a mono- or multi-filament wire that has the flexibility to easily bend and conform to various geometries yet stiff enough to create a self-supported snare loop that extends generally perpendicular to the long axis of the guide. Materials that may be used to construct the snare cord include plastics such as nylon, polyethylene, polyester or polypropylene or metals such as stainless steel or nitinol.

A plunger at the proximal end of the guide may be used to provide a counterforce when pulling on the slider. As the plunger is pushed and the slider is simultaneously pulled, the snares will move into the retracted position first, and then the expanding arms are retracted into the slender configuration. As the slider is released, the spring forces will extend the snares to the extended position and the expanding arms will be converted to the radially expanded condition.

In another embodiment, the snares may include a basket element to prevent the needle from traversing deeply into the abdominal cavity and causing potential harm.

The basic procedural steps of the utilization of the suturing system may flow as follows. At the end of the surgical procedure, the trocar is removed from the body exposing the wound. The slider on the guide is pulled up against the plunger to contract the flexing arms and retract the snares such that the profile of the guide is at its minimum. The guide can then be inserted into the wound with the plunger continually pulled against the slider. The slider and plunger are then released expanding the arms and deploying the snares. The guide can be pulled upward and away from the body cavity until the arms rest against the inner wall of the peritoneum. A short tail at one end of the suture is secured by the capture rod in the tip of the needle. The needle, with suture, is then passed through a first needle channel in the guide and is advanced through the guide, tissue and snare, into the abdominal cavity. The needle then releases the suture into the cavity, and is retracted from the body. A second short tail at the second free end of the suture is then secured by the capture rod in the needle. The needle, with suture, is then passed through the second needle channel in the guide and advanced through the guide, tissue and snare, into the abdominal cavity. The needle then releases the suture into the abdominal cavity and removed from the guide and body. The remaining loop of suture outside the body may then be released from each of the slots in the needle tracks. The slider on the guide is then again pulled against the plunger to retract the snares, capturing the free ends of suture, and contract the flexing arms allowing the guide to be removed from the wound, carrying the suture with it. Once outside the body, the snares may need to be deployed enough to release the free ends of the suture. Lastly, a knot may be tied and pushed down into the wound to close the trocar puncture site.

In an alternative procedure, the guide may be used to place a FIG. 8 stitch using two separate sutures rather than a single stitch using only one suture. The guide is initially inserted into the wound as previously described. A short tail at a first end of a first suture is loaded into the needle, passed through the first channel of the guide, and released into the abdominal cavity. At this point a short tail at the second end of the first suture is loaded into the needle, and passed through the second channel. The guide may then be rotated approximately 90 degrees from the initial orientation of the first suture passing. A short tail at one end of a second suture may be loaded into the needle, passed through the first channel of the guide, and released into the abdominal cavity. The needle is retracted and then a tail from the opposing end of the second suture is loaded and passed through the second channel of the guide and released into the abdominal cavity. The slider is pulled and the guide is removed from the wound with all four ends of suture captured in the snares. Knots may then be tied in each of the individual sutures to close the wound.

The basic procedural steps for abdominal entry and insufflation of the cavity may flow as follows. The needle is used to enter the abdominal cavity using standard closed laparoscopic techniques. A gas line is connected to the handle allow for an inert gas to be passed into the abdominal cavity. The inert gas is then turned on until the cavity reaches an appropriate level of insufflation to allow for the procedure to be performed with appropriate visualization. The needle is then removed, and a trocar is inserted into the puncture site to perform the procedure.

In an alternative embodiment, the guide may comprise a monolithic snare where the actuator section, shaft section and suture catchers, such as snare loops, are all integrally formed. The barrel may comprise two half barrel pieces that can be secured together. The barrel defines an inner lumen and at least two diagonal channels in communication with two corresponding window openings adjacent to a distal end of the barrel. Each channel comprises a wider proximal opening that tapers towards a distal exit so as to serve as a fulcrum for the needle apparatus directed therethrough. Each snare loop comprises a tip that may serve as a landmark indicator to position the guide against the internal peritoneal wall.

The snare loops can be completely retracted within the barrel by moving the actuator section and integral shaft section of the snare axially and proximally through the inner lumen. The enlarged tip of each snare loop comprises a positive stop abutting the narrower window opening within the barrel so as to prevent excess travel of the monolithic snare within the barrel.

The guide may comprise indicia on an outer barrel surface to indicate how far to insert the barrel into the abdomen (i.e., until the mark is no longer visible) so as to achieve a more optimal "bite," namely, the horizontal distance from the puncture location of the needle through the peritoneum to the closest edge of the defect coinciding with the sidewall of the barrel.

An alternative method is provided to achieve a desirable placement of the needle and suture through the tissue, particularly for thinner abdominal walls. Prior to the placing the needle though the tissue, the lateral tip of a snare loop may be used as a landmark while tilting the guide at an angle to the primary guide axis, until the first lateral tip comes in close proximity to or abuts the peritoneum. The tissue area will compress, and placement of the needle will encompassed a greater amount of tissue.

With the tilted guide in position, the suture engaging device, with a first free end section of suture engaged, may be inserted through a first channel while carrying the first section of suture. Once the needle exits the channel it passes through the compressed layers of tissue, and enters the body cavity. As it enters the body cavity, the needle passes through the first suture catcher, which may comprise a snare loop. The needle may release the strand of suture and be removed from the body leaving the suture section loosely inside the expanded snare loop. Thus, the suture section is carried into the body cavity to a point where the suture section intersects and traverses the generally planar opening defined by the expanded snare loop.

The guide is then tilted in the opposite direction, such that the opposite second lateral tip of the second suture catcher, such a second snare loop, comes in close proximity to the peritoneum. With the tilted guide in position, the second free end section of suture may then be engaged by the suture engaging device, and inserted through the opposing second channel to place the second end suture section. Once the needle exits the opposing channel it passes through the compressed layers of tissue and enters the body cavity. As it enters the body cavity, the needle passes through the opposing second suture catcher, e.g., snare loop. The needle may release the strand of suture and be removed from the body leaving the suture sections within the boundaries of the respective snare loops.

Moving the actuator section away from the barrel retracts the snare loops so as to capture the suture sections 542, 543. With both suture sections 542, 543 captured, the guide 530 is retracted from the tissue track, carrying the suture sections 542, 543. With the guide 530 and suture sections 542, 543 exposed outside the body cavity, the actuator section 533 can be pushed toward the barrel 531 extending the suture snare loops 534, and thus releasing the suture sections 542, 543. A knot can then be tied in the suture sections 542, 543 and secured to provide closure of the wound.

BRIEF DESCRIPTION OF THE DRAWINGS

FIG. 1 illustrates an oblique view of a preferred embodiment of a needle.

FIG. 2 illustrates a perspective side view of a proximal end of the needle.

FIG. 7 illustrates an oblique view of the distal tip of the guide with radially expanded arms and suture catchers.

FIG. 8 illustrates an oblique view of the guide reveals pathways for suture passing.

FIG. 13A illustrates a perspective side view of the insertion of the needle with second end of suture strand into the guide.

FIG. 13B illustrates a perspective side view of an enlarged view of the insertion of the needle with second end of suture strand into the guide.

FIG. 19A illustrates an exploded view of the guide.

FIG. 19B illustrates an isometric view of the guide.

FIG. 21A illustrates an isometric view of the guide with the snare retracted.

FIG. 21B illustrates a detail view of the distal end of the guide with the snare retracted.

FIG. 28A illustrates isometric view of the guide placed deeper in the wound.

FIG. 28B illustrates detail view of the guide with the line mark positioned in the wound.

FIG. 28C illustrates detail view of the guide with the lateral tip positioned in the wound.

Figure 3:
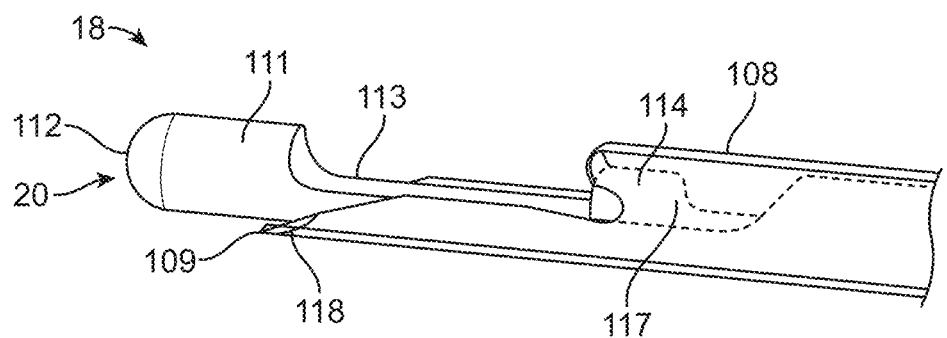
FIG. 3 illustrates a perspective side view of a distal end of the needle.

The various embodiments of the invention can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS

In a preferred embodiment, a system is provided for closing trocar wound sites. The system comprises a suture engagement device and a guide to direct the device through the body tissues.

An improved needle and guide instrument set is further described below as it allows for the surgical placement of suture to be completed "blind," namely, without the aid of an endoscope for direct visualization of the abdominal cavity. This may be advantageous in certain surgical procedures where an endoscope is not being used or does not provide adequate visualization of the surgical site.

A preferred embodiment of a suture engagement device or suture passing needle, or simply needle, 100 is shown in FIG. 1. The needle 100 may simply have a handle 101 and actuator 105 at the proximal end 12. An outer tube 108 is connected to the handle 101 that terminates with a suture capture mechanism 107, sharp needle tip 109, and spring loaded safety tip 112 at the distal end 14 of the needle 100, as shown in FIG. 3.

FIG. 2 illustrates a closer view of the proximal portion 16 of the needle 100. The base of the proximal end 12 of the needle 100 is a main handle or housing 101. The handle 101 may have a finger loop 102 that may accommodate one or more fingers, as well as a series of one or more grooves 103 to accommodate the placement of additional fingers. The finger loop 102 and grooves 103 may provide the user with a comfortable, secure grip of the device and provide greater control when handling the device 100. Slidably disposed within the housing 101 is an actuator 105 that may be used to control a suture capture mechanism 107 at the distal tip of the needle 101. At the proximal end of the actuator 105, an enlarged surface 106 may provide an ergonomic location for a thumb or other finger to trigger the actuator 105. The length travel of the actuator 105 may be constrained by a pin 123 that connects to the actuator 105 and slides within a slot 104 on the handle 101. The pin 123 also serves the purpose of rotationally constraining the actuator 105.

FIG. 3 illustrates a closer view of the distal portion 18 of the needle 100. An obturator tube 111 may be slidably disposed within an outer tube 108, and a capture rod 114 may be slidably disposed within the obturator tube 111. The outer tube 108 terminates at a sharp tip 109 that may have two or more beveled edges 118 to facilitate the ease of passage of the needle 100 through tissue. The obturator tube 111 has a blunt surface 112 at its distal end 20 and may be used to serve as a safety tip for the needle 100. The obturator tube 111 may be spring loaded such that it can passively travel between an axially extended and retracted position. Initially, the obturator tube 111 may be biased in the extended position where the blunt surface 112 extends further distally than the sharp tip 109 of the outer tube 108. As the distal tip of the needle 100 is pushed into the tissue with enough load to overcome the force of the spring, the obturator tube 111 may retract proximally, ultimately exposing the sharp tip 109 of the outer tube 108. The sharp tip 109 and edges 118 may then minimize the trauma to the tissue layers as the needle 100 is inserted. Once the tip 109 of the needle 100 enters the body cavity, the obturator tube 111 may passively return to the distally extended position shielding the sharp tip 109 from inadvertently damaging the tissue structures within the body cavity. The purpose of the capture rod 114 is to secure the suture to the needle 100, in a manner further described below.

Figure 4A:
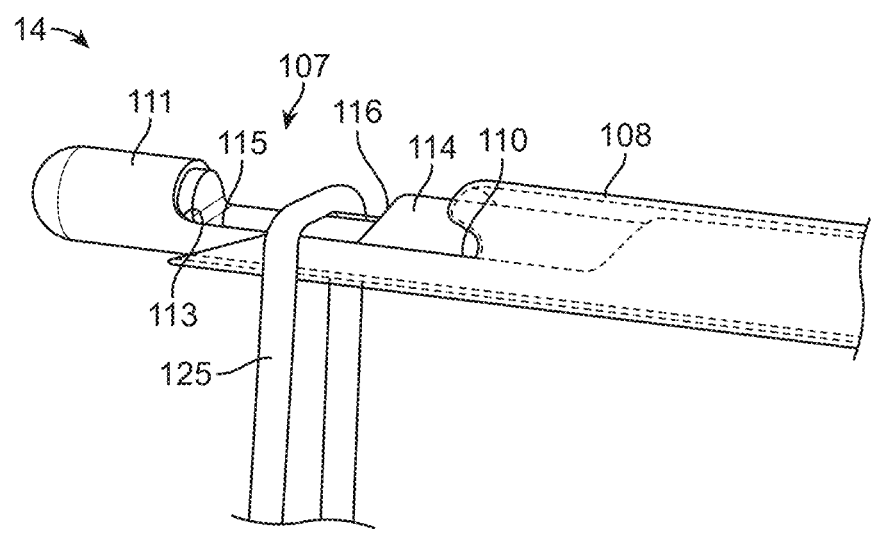
FIG. 4A illustrates a perspective side view of a strand of suture being loaded into the needle with an extended capture rod.
Figure 4B:
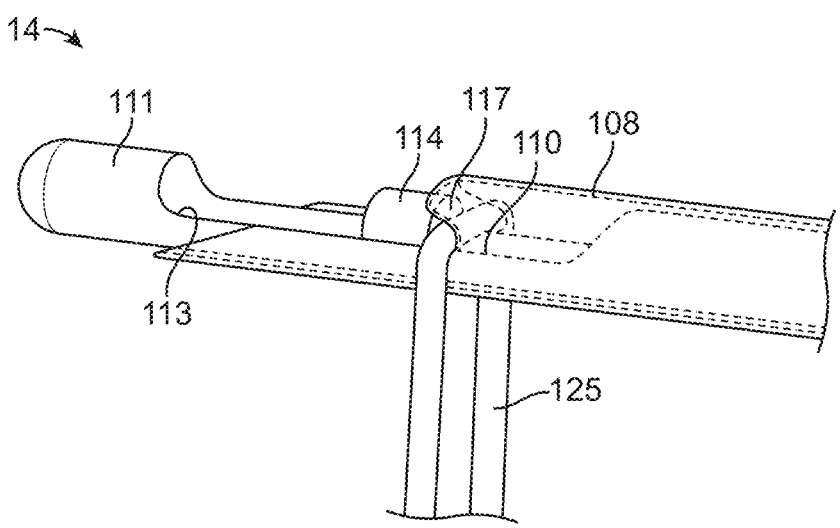
FIG. 4B illustrates a perspective side view of a strand of suture captured by the needle after retraction of the capture rod.

In FIGS. 4A and 4B, the suture capture mechanism 107 at the distal end 14 of the needle 100 preferably comprises a channel 110 in the outer tube 108, a cutout section 113 of the obturator tube 111, and a slot 115 in a capture rod 114. The suture capture mechanism 107 may function through the movement of the capture rod 114 between an axially extended and retracted position that is controlled by the actuator 105 at the proximal end 12 of the needle 100. In FIG. 4A, the capture rod 114 is shown in the extended position such that a strand of suture 125 can be placed through the cutout 113 in the obturator 111 and into the slot 115 of the capture rod 114. In this axially extended position, the obturator cutout 113 is open to, and aligned with, the capture rod slot 115 in order to receive the suture 125. In FIG. 4B, the capture rod 114 is shown in the axially retracted position such that the strand of suture 125 is secured between the channel 110 of the outer tube 108 and the distal face 117 of the slot 155 in the capture rod 114. When the suture 125 needs to be released, the actuator 105 returns the capture rod 114 to the extended position. A proximal face 116 of the capture rod 114, shown in FIG. 4A, may aid in pushing the suture 125 out of the obturator cutout 113 and away from the outer profile of the outer tube 108.

Figure 5A:
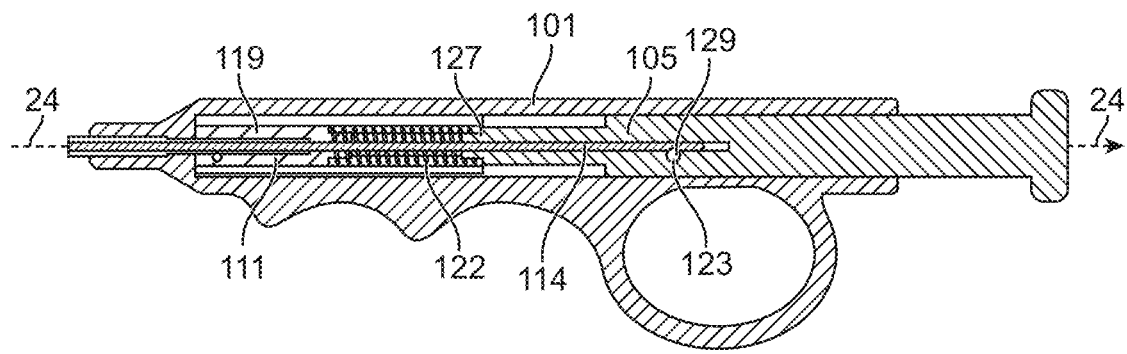
FIG. 5A illustrates a cross-sectional view of the needle demonstrating the internal components.
Figure 5B:
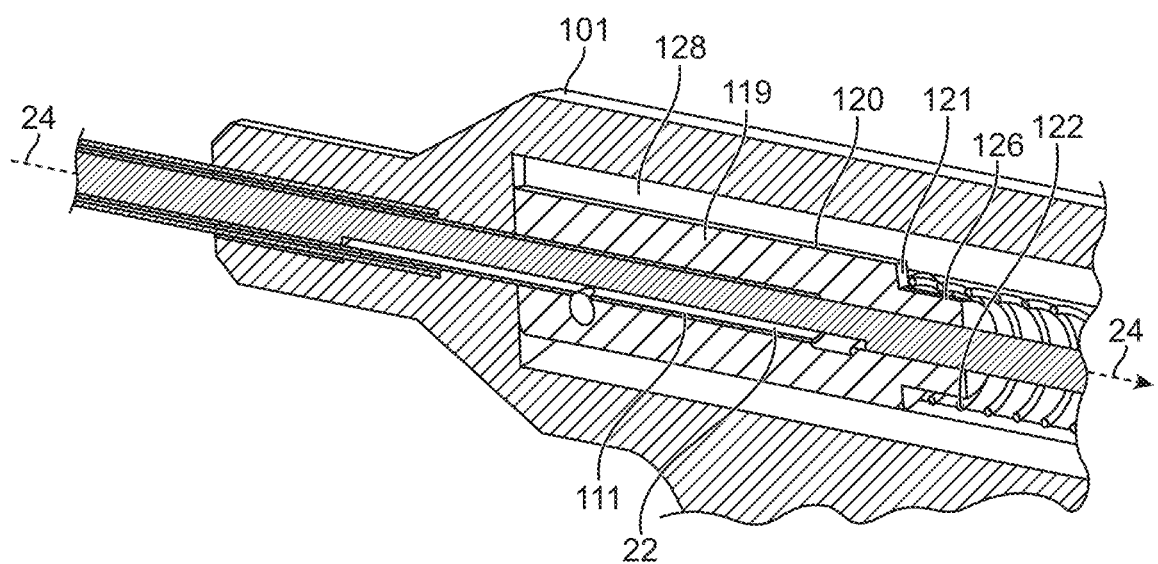
FIG. 5B illustrates a cross-sectional view of the needle demonstrating the inner workings of a needle handle.

Cross sectional views of the preferred embodiment of the needle 100 are shown in FIGS. 5A and 5B that illustrate the inner workings of the handle 101. A proximal portion 22 of the obturator tube 111 may be connected to an obturator hub 119. The hub 119 may have one or more rotational alignment structures such as a flat face 120 or an alignment post 121 that prevent the hub 119 from rotating about a long axis 24 as it translates back and forth. Additional extrusions 128 inside the housing 101 may be necessary to mate with the alignment protrusions 120, 121 on the hub 119. The alignment of the hub 119 is critical to ensure the cutout 113 at the distal end maintains its alignment for suture capturing. The hub 119 may also have a cylindrical portion 126 to accommodate a coil spring 122 that is used to spring load the obturator tube 111. The opposing end of the spring 122 may connect to the actuator 105 at a similarly accommodating cylindrical portion 127. The capture rod 114 may be attached to the actuator 105 with a pin 123 that passes through a hole 124 in the actuator and a slot 129 in the capture rod. As previously described, the pin 123 may slide within a window 104 of the housing 101 that is used to limit the travel and prevent rotation of the capture rod 114.

Figure 6A:
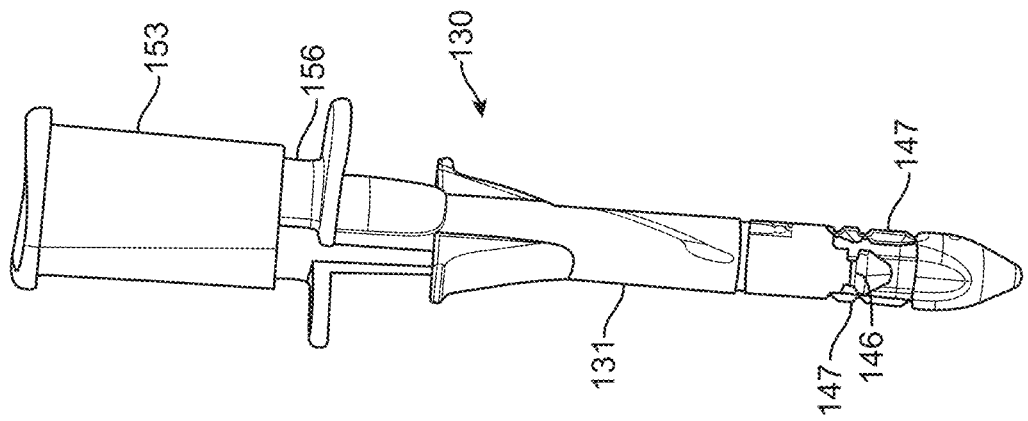
FIG. 6A illustrates an oblique view of the guide with radially expanded arms and suture catchers.
Figure 6B:
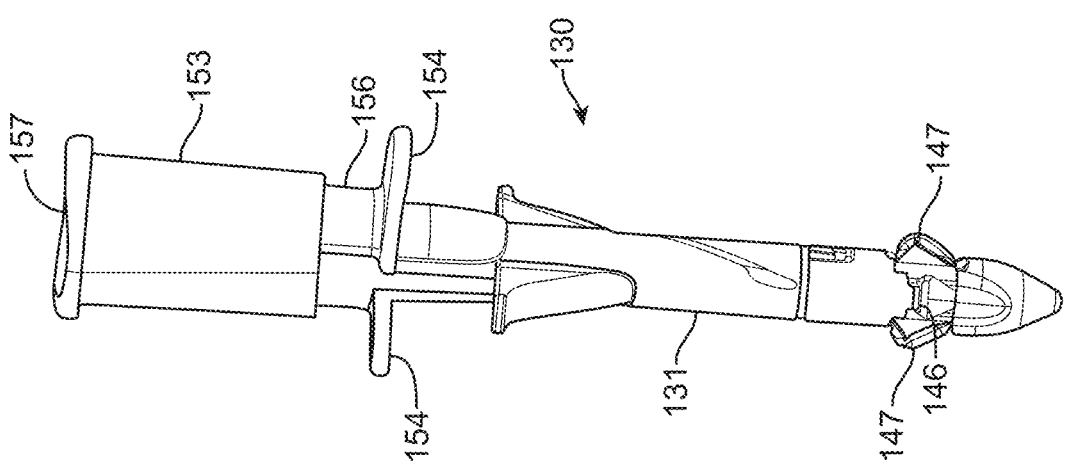
FIG. 6B illustrates an oblique view of the guide with radially expanded arms and contracted suture catchers.
Figure 6C:
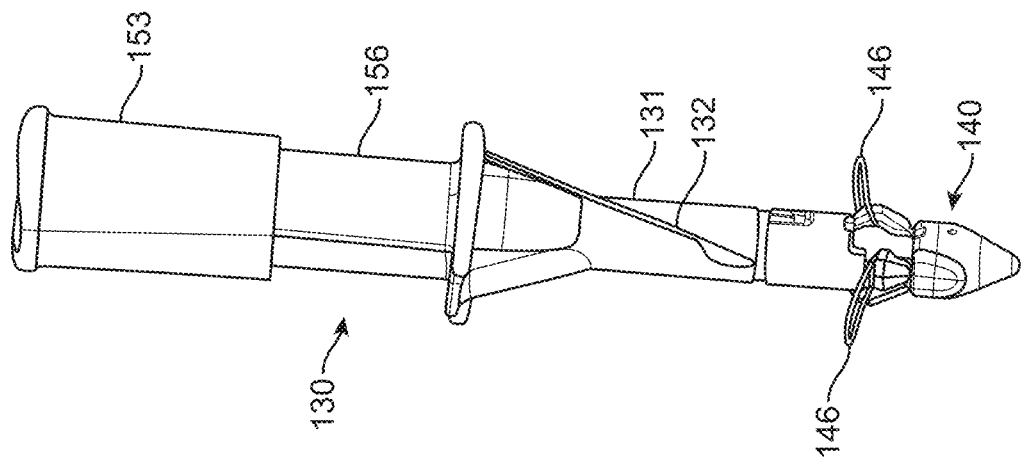
FIG. 6C illustrates an oblique view of the guide with radially contracted arms and suture catchers.

In FIGS. 6A-6C, a preferred embodiment of a guide 130 may be useful for directing the above described suture engaging device through a body wall. The guide 130 may be particularly useful for the placement of sutures used in closing wounds or openings through body walls made in surgical procedures to access internal body cavities. Accordingly, the guide 130 preferably comprises two pathways diagonal to each other and oriented to direct a needle apparatus to both a first internal location to carry and release a first end of a suture, and a second internal location to carry and release a second end of a suture.

Figure 12:
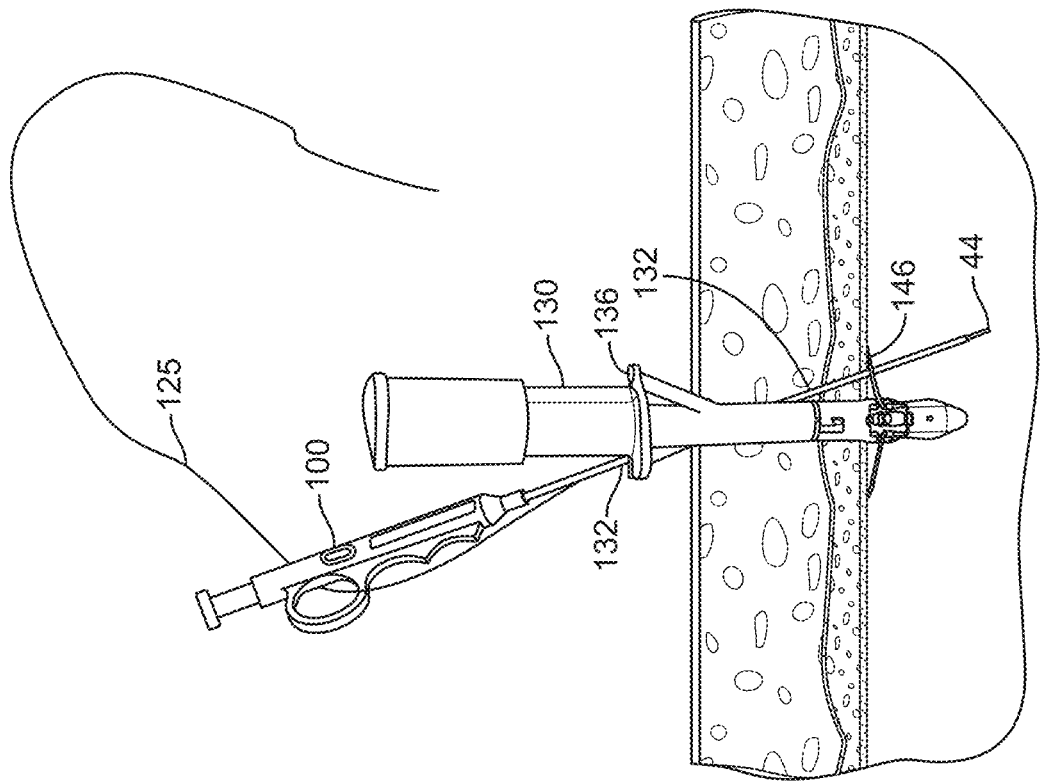
FIG. 12 illustrates a perspective side view of the insertion of the needle with first end of suture strand into the guide.

An oblique view of the preferred guide 130 is shown in FIGS. 6A-6C. The guide 130 may comprise a distal barrel tip 140 with two radially expanding arms 147, two suture capturing mechanisms, or suture catchers, which may comprise snare loops 146 in this illustrated embodiment, a main barrel 131 with two channels 132, 136 (shown in FIG. 8), a plunger 153, and a slider 156. The two channels 132, 136 are disposed within the main barrel 131 to guide the suture passing needle 100 through the tissue to be sutured, as shown in FIGS. 8 and 12. The slider 156 may be slidably disposed onto the main barrel 131 to provide actuation of the suture snare loops 146. The plunger 153 may be slidably disposed onto the main barrel 131 to provide actuation of the expanding arms 147. The expanding arms 147 may serve as an internal cavity securing mechanism, which is used to secure the guide 130 against the internal peritoneal wall. The two suture snare loops 146 serve the purpose of capturing the suture material after it has been passed through the tissue wall. The slider 156 may facilitate the ease of handling of the guide 130.

As the slider 156 translates with respect to the barrel 131, the suture snare loops 146 move between two positions of radially extended shown in FIG. 6A and retracted shown in FIG. 6B. When each snare 146 is in the radially extended configuration, a loop, ring, circle or hoop shape is preferably formed. The snare loop 146 provides a region for a suture passing needle to pass into and drop off the suture. The snare loop 146 defines an opening through which the carried suture traverses. When the carried suture is released from the suture engaging device, the suture section intersecting the opening of the snare loop 146 resides loosely until the snare loop 146 is retracted. When the snare loop 146 is retracted the suture material becomes trapped between the snare loop 146 and the wall of the distal barrel tip 140.

Further, as the plunger 153 translates with respect to the barrel 131, the radially expanding arms 147 at the distal barrel tip 140 move between two positions of radially expanded, or flared out, as shown in FIG. 6B, and radially contracted, or slender, as shown in FIG. 6C. Each of the expanding arms 147 preferably comprise a living hinge section, where the material is cut thin at specific locations allowing for the material to flex. It is to be expressly understood that the expanding arms may comprise a variety of structures and mechanisms that are capable of moving between slender and flared out configurations.

As shown in FIG. 7, radially adjacent to the expanding arms 147 may be one or more distally extending stop tabs 143. The stop tabs 143 are configured to provide a mechanical stop for the distal end cap 141 of the barrel tip 140 to collide against preventing excessive flex within the thin sections 148, 149, 150 of the expanding arms 147. The stop tabs 143 may also have a slot 145 cutout in the outer wall that provide a region for the snare loop material 146 to be housed when the snare loop 146 is in the retracted state. When a section of suture 159 is captured within the snare loop 146, the slot 145 may provide additional security to the captured suture 159, as opposed to the snare loop 146 pulling the suture against a smooth surface.

The barrel tip 140 may comprise a separate component that is assembled to the main barrel 131. Two tabs 166 on the main barrel 131 may be placed radially opposite to each other. Slots 167 in the barrel tip 140 may allow for the tip 140 to initially slide past the tabs 166 on the main barrel 131. The slots 167 may have an undercut section 168 that may be engaged by rotating the tip 140 and pulling it distally. The gap that is created between the tip 140 and the barrel 131 may be filled with a deformable c-shaped clip 169 to prevent the tip 140 from dislodging from the barrel 131.

The slider 156 is slidably disposed on the main barrel 131 as it can travel between a distal position shown in FIG. 6A and a proximal position shown in FIG. 6B. Two finger tabs 154 are preferably disposed near the distal end of the slider 156 and configured to be grasped with one or more fingers. The thumb or palm of the hand may then be pressed against the proximal face 157 of the plunger 153. The finger tabs 154 may then be pulled proximally to actuate the guide 130 with the plunger 153 being used to provide a counterforce. The slider 156 can reach a stop, achieved by either an internal feature of the slider 156 engaging the main barrel 131 or the snare loops 146 being fully retracted. Additional force between the slider 156 and the plunger 153 may overcome the counterforce translated to the plunger 153 by a spring. The plunger 153 can then move axially to actuate the expanding arms 147 to the slender contracted state. Upon release of the force between the slider 156 and the plunger 153, the plunger 153 can return to the original position and result in the expanding arms 147 reverting to the radially expanded position. The slider 156 may be biased to the distal position by a spring that passively returns the slider 156 to the distal position when released, thus resulting in the suture loops 146 reverting back to the radially extended position. It may be appreciated that biasing the guide 130 in this configuration may allow for the surgeon to have his hands free from operating the guide 130 such that work with other instruments may be conducted once the guide 130 has been inserted into the trocar wound.

In the preferred embodiment, the guide 130 provides two different, diagonal pathways for a suture passing needle apparatus and thus comprises first and second channels 132, 136 as more clearly shown in FIG. 8. The channels 132, 136 are directionally diagonal to the long axis "24" of the guide 130 at some acute angle, preferably in the range of 5-30 degrees. The angle of the channels 132, 136 controls the depth of bite into the tissue, such that a greater angle provides a greater bite of tissue. Angular spacing between entries to the channels 132, 136 are preferably equal (i.e., equiangular) depending upon the number of channels, e.g., 180 degrees apart if there are two channels, 120 degrees apart if there are three channels, etc. Two separate entry points 133, 137 are provided on the channels 132, 136 for a suture passing needle to enter the guide 130, as well as two separate exit points 134, 138. Each channel 132, 136 has a slot 135, 139, or opening that allows for a strand of suture to be removed from the channel. This may be necessary to complete the suture loop in the tissue.

Figure 9A:
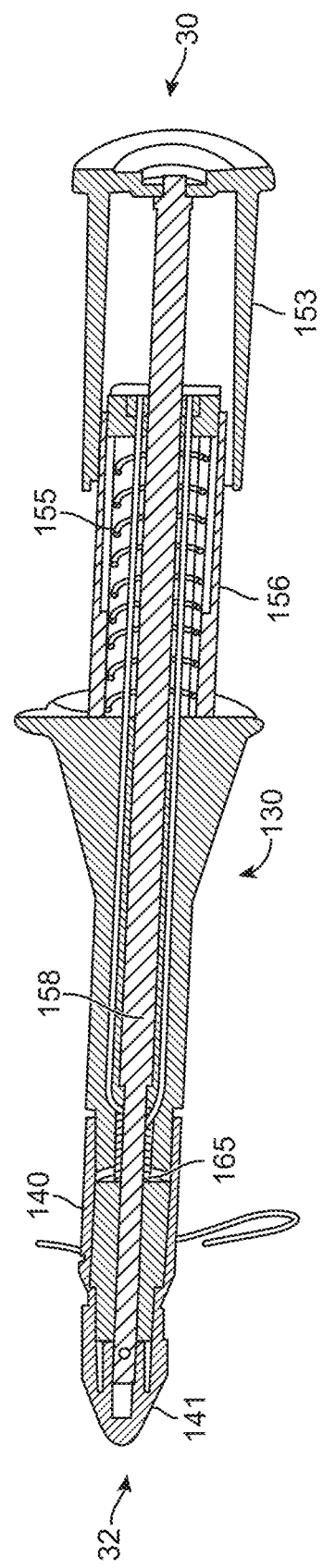
FIG. 9A illustrates a cross-sectional view of the guide showing internal components.
Figure 9B:
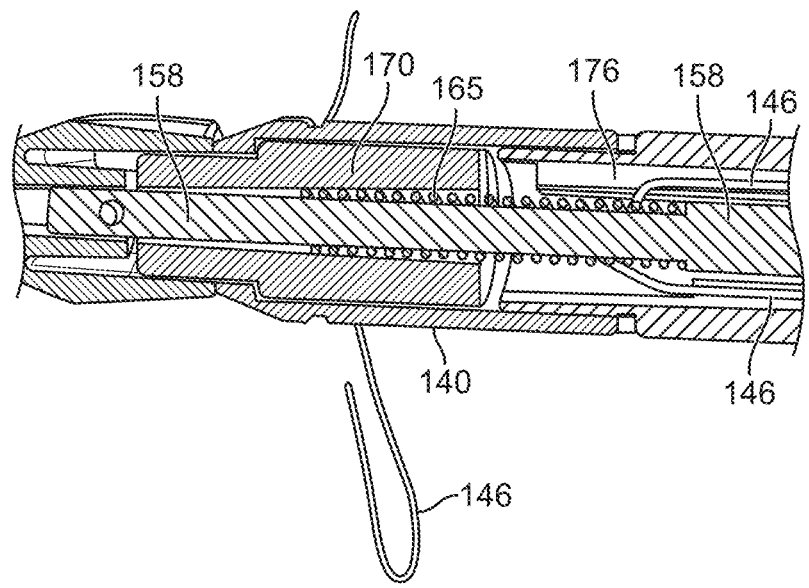
FIG. 9B illustrates an enlarged cross-sectional view of the guide showing distal internal components.
Figure 9C:
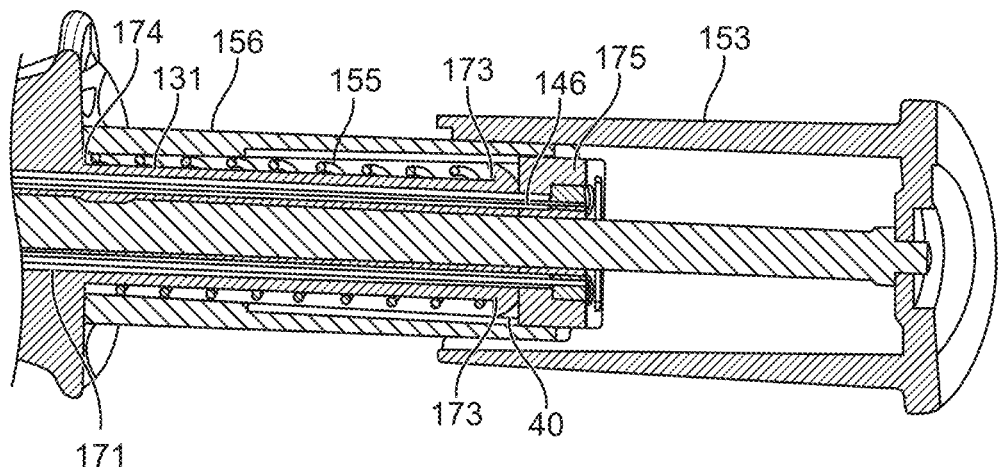
FIG. 9C illustrates an enlarged cross-sectional view of the guide showing proximal internal components.

The internal workings of the guide 130 are shown in FIGS. 9A-9C, which illustrate cross-sectional views through the center of the guide 130. An inner shaft 158 spans from the proximal end 30 to the distal end 32 of the guide 130 and is used to actuate the expanding arms 147. The shaft 158 connects at the distal end 32 of the guide 130 to the distal end cap 141 of the barrel tip 140, and connects at the proximal end 30 of the guide 130 to the plunger 153. A retaining ring, heat stake, or other mechanical fastening means may be used to secure the shaft 158 to the plunger 153. When the slider 156 is pulled into the proximal position as shown in FIG. 6B, a counterforce is applied to the plunger 153. Upon the slider 156 reaching the full proximal extension, further pushing on the plunger 153 advances the shaft 158 distally which in turn advances the end cap 141 on the barrel tip 140 distally, causing the expanding arms 147 to radially contract as shown in FIG. 6C. Upon release of the plunger 153 and slider 156, the shaft 158 may passively return to its native proximal position, pulling the end cap 141 with it and causing the expanding arms 147 to radially extend.

Two springs are used to bias the guide 130 into the configurations shown in FIGS. 6A and 9A, with the radially extended arms 147 and snare loop 146 expanded, and the plunger 153 in the proximal position. A slider spring 155 is used to bias the slider 156 to the proximal position. In FIG. 9C, one end of the slider spring 155 is captured at the proximal end 40 of the main barrel 131 by two spring capture tabs 173. The opposing end of the spring 155 rests against an inner edge 174 of the slider 156, forcing the slider 156 to a proximal position. In FIG. 9B, a plunger spring 165 is used to bias the distal barrel tip 140 in the proximal position. The spring 165 is captured between inner shaft 158 and the proximal face of track support 170 connected to the barrel tip 140. This plunger spring 165 forces the inner shaft 158 and plunger 153 in a proximal position, pulling the barrel tip 140 proximally as well.

In FIG. 9C, the free ends of a snare cord loop 146 may be captured in a retaining cap 175 that is fixed to the proximal end of the slider 156. The snare cord 146 may traverse distally down the guide 130 either through snare channels 176 inside the main barrel 131 or guide tubes 171 that span through a portion of the length of the main barrel 131. The snare channels 176 or guide tubes 171 may be used to constrain the snare cord material 146 and prevent it from bunching up or buckling under load as it travels proximally and distally within the guide 130.

Figure 10A:
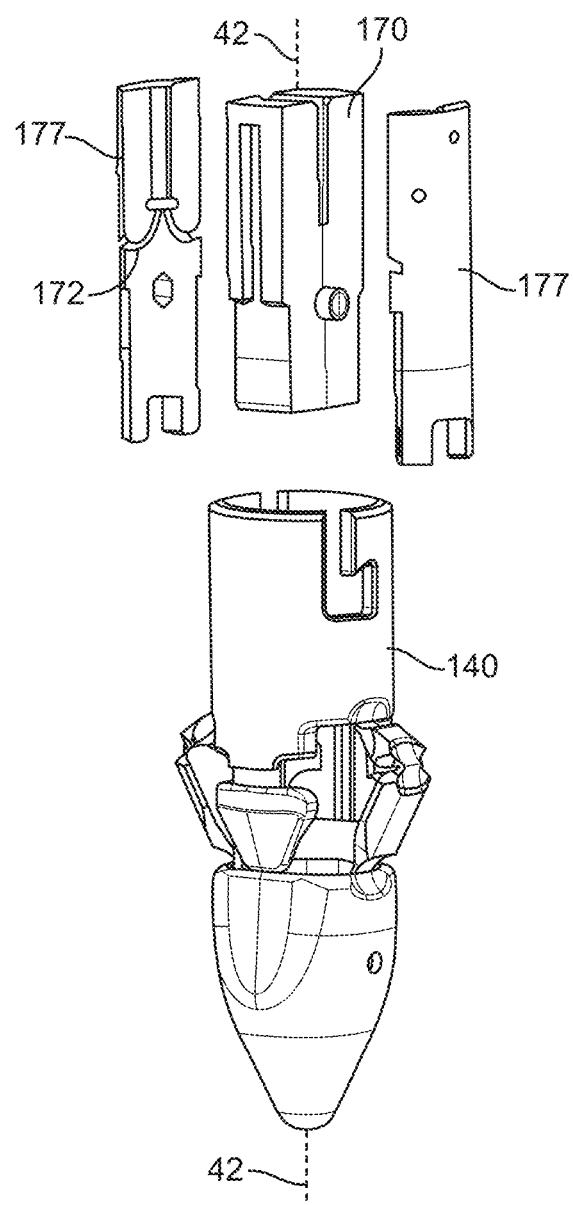
FIG. 10A illustrates an exploded view of barrel tip components.
Figure 10B:
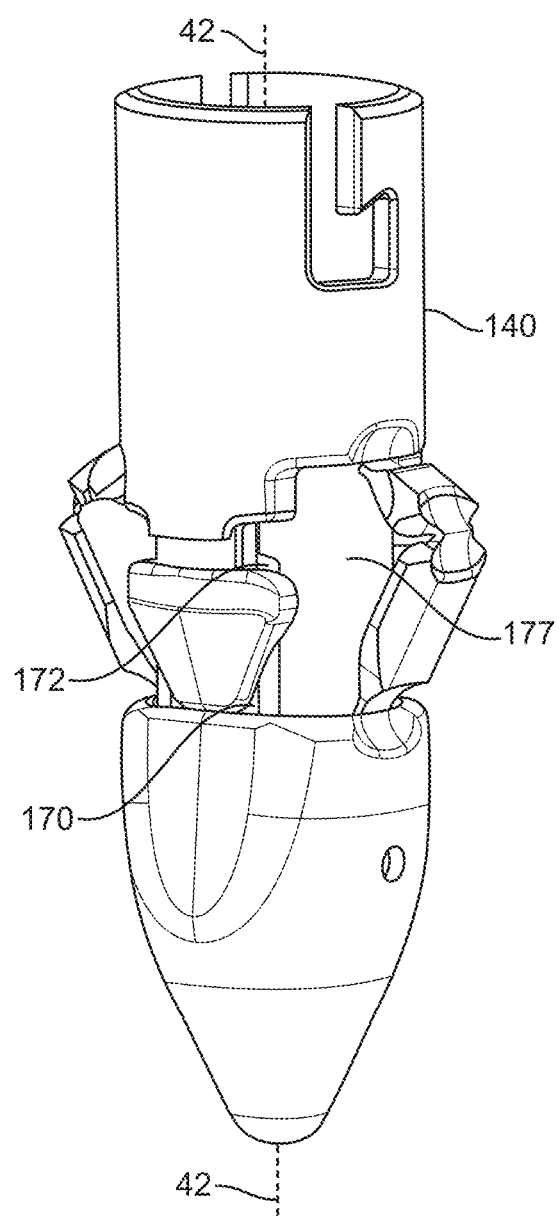
FIG. 10B illustrates an isometric view of barrel tip components.

FIGS. 10A-10B illustrate the laminate component construct that provides tracks 172 within the barrel tip 140. The track support 170 is positioned between two track side panels 177. The tracks 172 may be used to guide the snare cord 146 from a position within the barrel tip 140, parallel to the long axis of the guide 130 to a position exiting the barrel tip 140 relatively perpendicular to a long axis 42 of the guide 130. These curved exit tracks 172 may take on an angulation of approximately 90 degrees, however this angle may be made more acute or obtuse to optimize the positioning of the snare.

Figure 11:
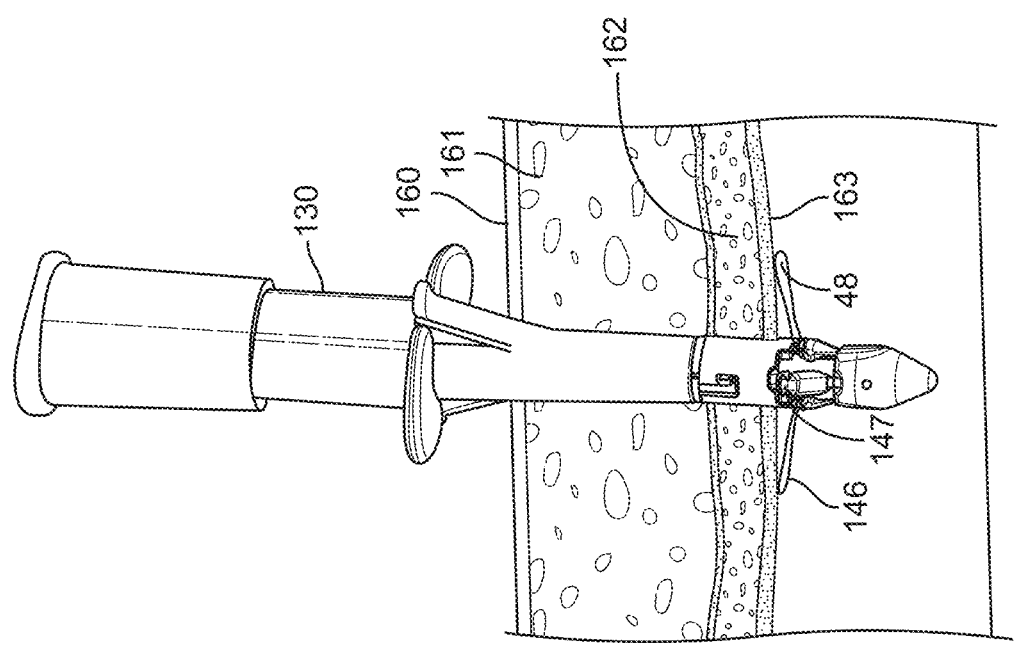
FIG. 11 illustrates a perspective side view of the insertion of guide into tissue.

In the case of a laparoscopic surgery involving use of a trocar, the guide 130 may be placed through the tissue layers of the open trocar wound site as shown in FIG. 11. This tissue track may consist of skin 160, adipose tissue 161, muscle and fascia 162 and the peritoneum 163. Prior to insertion of the guide 130 through the tissue track, the slider 156 and plunger 153 may be pulled into the compressed position to place the arms 147 in the slender configuration, and the snare loops 146 in the retracted position. Once the distal barrel tip 140 of the guide 130 is appropriately placed posterior to the peritoneal layer 163, the slider 156 and plunger 153 may be released and spring-biased to the open position, extending the suture snare loops 146 and expanding the tissue engaging arms 147. The guide 130 may then be retracted until the tissue engaging arms 147 are resting against the inner peritoneal wall 163 to align the channels 132, 136 with the appropriate layers of tissue to be sutured.

Once the guide 130 is secured against the peritoneal wall 163, the suture engaging device 100, with a first free end section 44 of suture 125 engaged, may be inserted through a channel 132 while carrying the section 44 of suture 125, as shown in FIG. 12. Once the needle 100 exits the channel 132 it passes through various layers of tissue 162, 163 and enters the body cavity. As it enters the body cavity, the needle 100 passes through the snare loop 146. The needle 100 may release the strand of suture 125 and be removed from the body leaving the suture section 44 loosely inside the expanded snare loop 146. Thus, the suture section 44 is carried into the body cavity to a point where the suture section 44 intersects and traverses the generally planar opening 48 (see FIG. 11) defined by the expanded snare loop 46.

The second free end section 46 of suture 125 may then be engaged by the suture engaging device 100, and inserted through the opposing channel 136 to place the second end suture section 46. As shown in FIGS. 13A-13B, once the needle 100 exits the channel 136 it passes through various layers of tissue 162, 163 and enters the body cavity. As it enters the body cavity, the needle 100 passes through the opposing snare loop 146. The needle 100 may release the strand of suture 125 and be removed from the body leaving the suture sections 44, 46 within the boundaries of the respective snare loops 146.

Figure 13C:
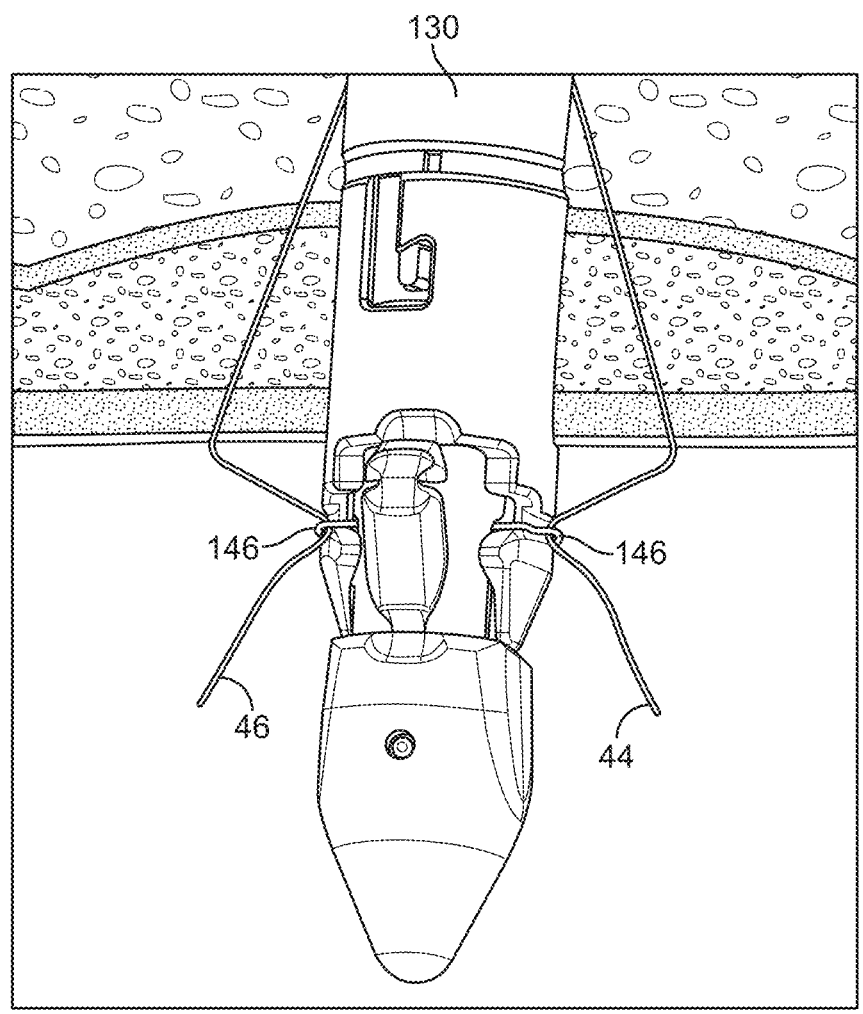
FIG. 13C illustrates a perspective side view of the guide with the suture catchers retracted so as to capture the suture sections.
Figure 13D:
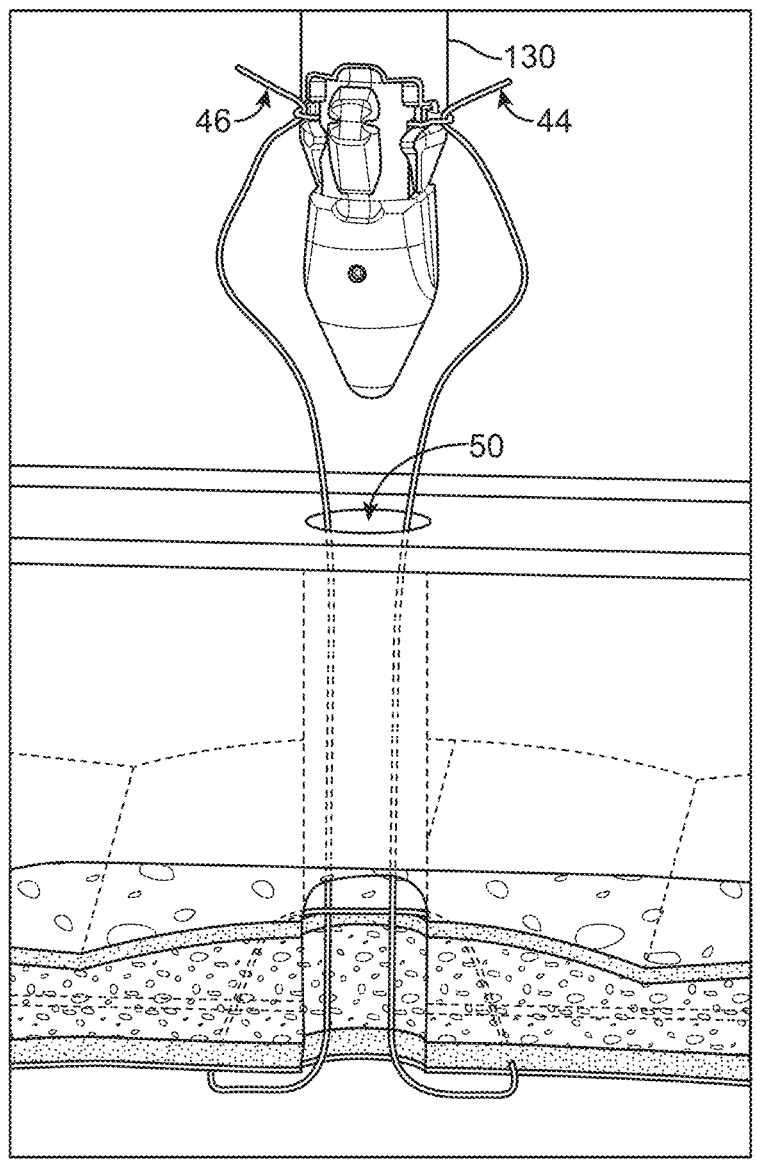
FIG. 13D illustrates a perspective side view of the guide retracted out from the tissue track with the captured suture sections.

FIG. 13C shows the snare loops 146 retracted so as to capture the suture sections 44, 46, which is the configuration actuated in FIG. 6B when the slider 156 is moved proximally with respect to the main barrel 131. With both suture sections 44, 46 captured, the guide 130 is ready to be retracted from the tissue track 50, carrying the suture sections 44, 46 as shown in FIG. 13D.

Figure 14:
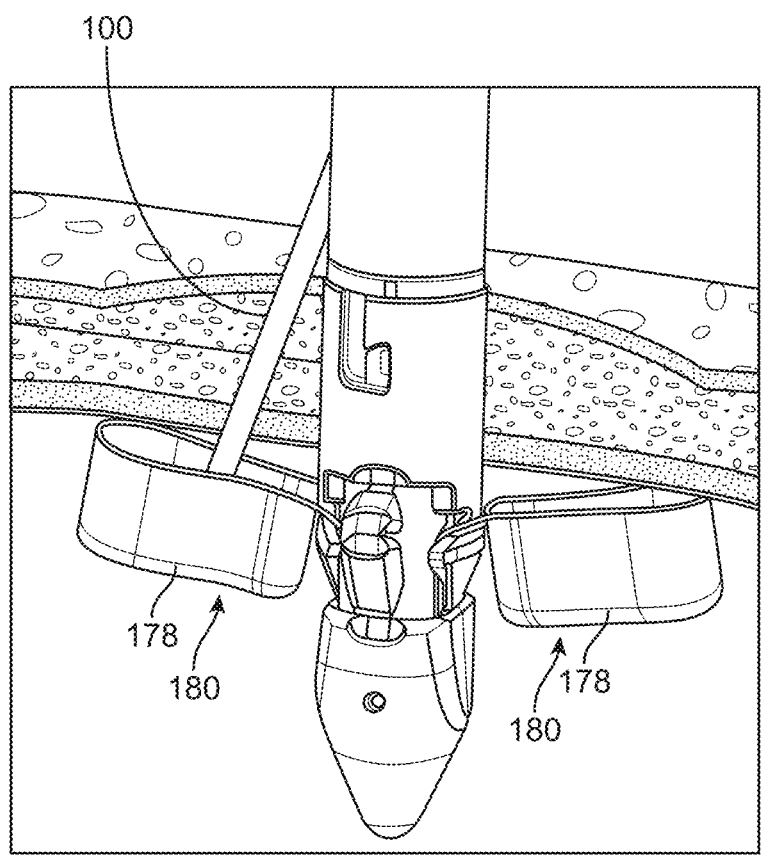
FIG. 14 illustrates an isometric view of snare with protective basket.

FIG. 14 illustrates an alternative embodiment including a pouch, or basket, 178 secured to the snare. The pouch 178 is positioned below the snare and comprises a floor 180 as a protective element to prevent the distal tip of the needle 100 from extending deeper into the abdominal cavity. The pouch may be constructed of a compliant fabric, rigid polymer, or other such material to obstruct needle penetration.

Figure 15:
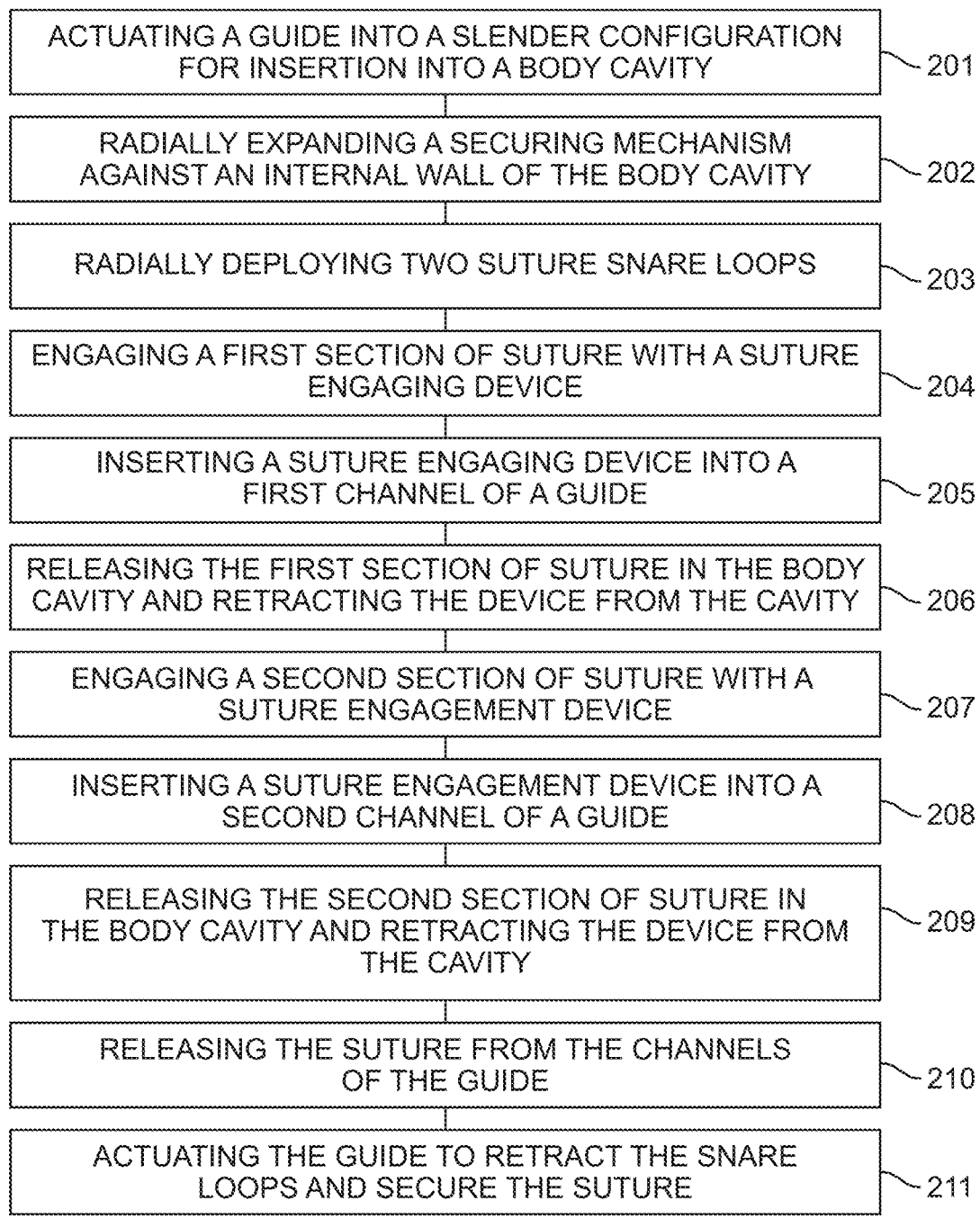
FIG. 15 illustrates a preferred method for closing a surgical wound with a single stitch using a system comprising preferred embodiments of a guide and a suture engaging device disclosed above.
Figure 15:
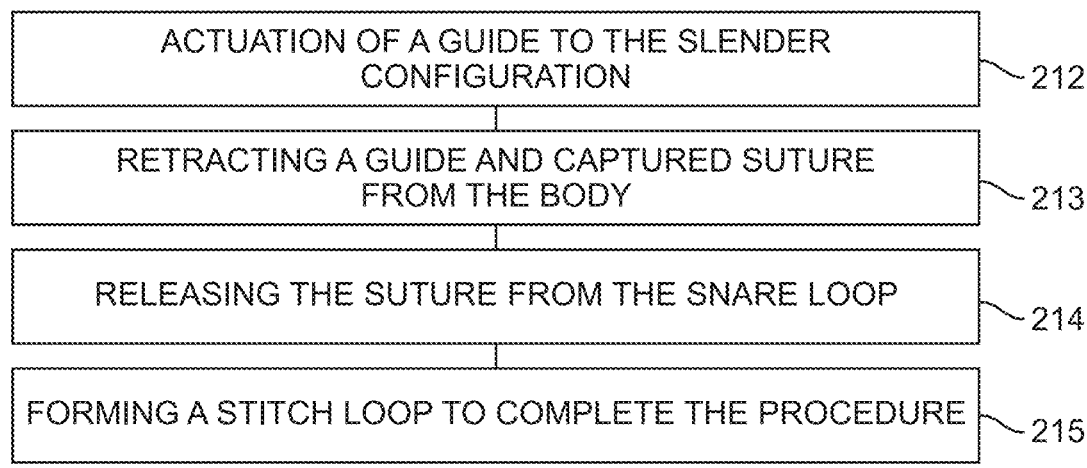

In FIG. 15 a preferred method 200 is disclosed for closing a surgical wound using a surgical instrumentation system comprising a guide and suture engagement device as described above. It will be appreciated that this method 200 enables an operator to pass and retrieve the suture using simply a guide and suture engaging device without the need for additional instrumentation or visualization inside the body cavity. The initial step 201 comprises actuation of the guide into a slender configuration and insertion of the distal tip into the surgical wound. In step 202, a securing mechanism, which may comprise living hinges, is radially expanded for engagement with the inner body cavity wall when the guide is retracted, preventing the guide from being pulled out of the wound as well as providing a reference point for the suture placement. Step 203 comprises the deployment of two suture catchers, which may preferably comprise snare loops, to be used to capture the suture material. It can be appreciated that step 202 and 203 may be combined such that they occur simultaneously. It will further be appreciated that steps 202 and 203 may occur by default (e.g., through use of springs) upon release of the guide such that the operator may have both hands free to engage other instruments.

Step 204 comprises engaging and capturing a first section of a suture with a suture capture mechanism disposed at the distal end of a suture engaging device having a shaft. In step 205 the suture engaging device with secured suture is inserted through a first track of the guide, through various tissue layers, and ultimately ending inside the body cavity as it passes through the first snare loop. Step 206 comprises releasing the first suture section from the suture engaging device and retracting the device from the body and guide. The first section of the suture may remain inside the body cavity and loosely encapsulated within the boundaries of the expanded first snare loop.

Step 207 comprises engaging and capturing a second section of the same suture with the suture capture feature on the suture engaging device. In step 208, the suture engaging device with secured suture is inserted through a second track of the guide, through various tissue layers, ending inside the body cavity as it passes through the second snare loop. Step 209 comprises releasing the suture from the suture engaging device and retracting the device from the body and guide while leaving the second section of the suture inside the body cavity and loosely encapsulated within the boundaries of the second snare loop.

In step 210, the suture material may be passed through the slots in the channels on the guide to release the suture from the constraint of the channel. Step 210 comprises retracting the snare loops back against the guide and securing the suture between the outer guide wall and the snare loop. In step 211, the guide may be actuated such that the securing mechanism is radially contracted and converting the guide into the slender configuration. It can be appreciated that step 210 and 211 may be combined such that they occur simultaneously or seamlessly with a single motion. In step 213 the guide can be removed from the body cavity with the two captured sections of the suture. Step 214 comprises releasing the suture from the snare loops on the guide. The procedure may then be completed at step 215 by forming a single stitch loop to close the surgical wound.

Figure 16:
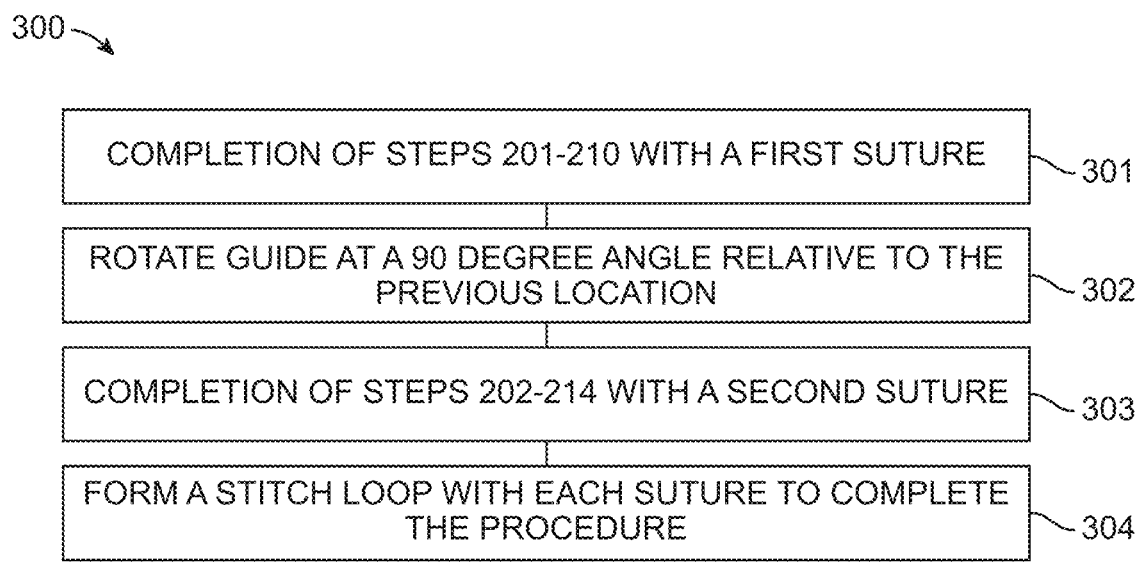
FIG. 16 illustrates a preferred method for closing a surgical wound with a figure eight stitch using the preferred system disclosed above.

In FIG. 16 an alternative method 300 is illustrated for closing a surgical wound using a surgical instrumentation system by forming a figure eight stitch as opposed to the single stitch method 200. In step 301 a first length of suture is passed into the body at a first location of the wound comprising the same steps 201-210 as previously described. In step 302, the guide is rotated 90 degrees from the initial position in step 301. In step 303, a second length of suture is passed into the wound at a second location of the wound comprising steps 202-214. Step 304 comprises completing the closing of the wound by forming a stitch loop with each of the suture strands.

Figure 17:
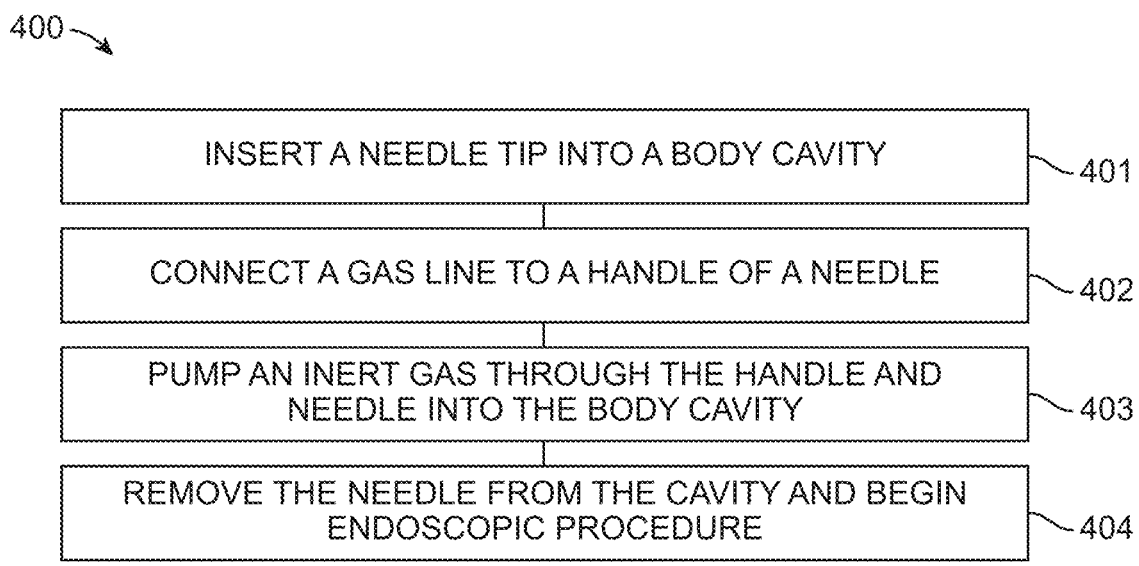
FIG. 17 illustrates a preferred method for creating pneumoperitoneum for laparoscopic procedures using an insufflation needle.

In FIG. 17 a preferred method 400 is illustrated for creating pneumoperitoneum for laparoscopic procedures using an insufflation needle. Step 401 comprises inserting the tip of the needle through the abdominal wall and into a body cavity. This step may also initially require a small incision in the skin to be made prior to insertion of the needle. In step 402, a gas line may be connected to the needle. Step 403 comprises pumping an inert gas through the needle and into the body cavity until an appropriate internal pressure is achieved. Lastly, in step 404 the needle may be removed from the body and the endoscopic procedure can begin.

Figure 18:
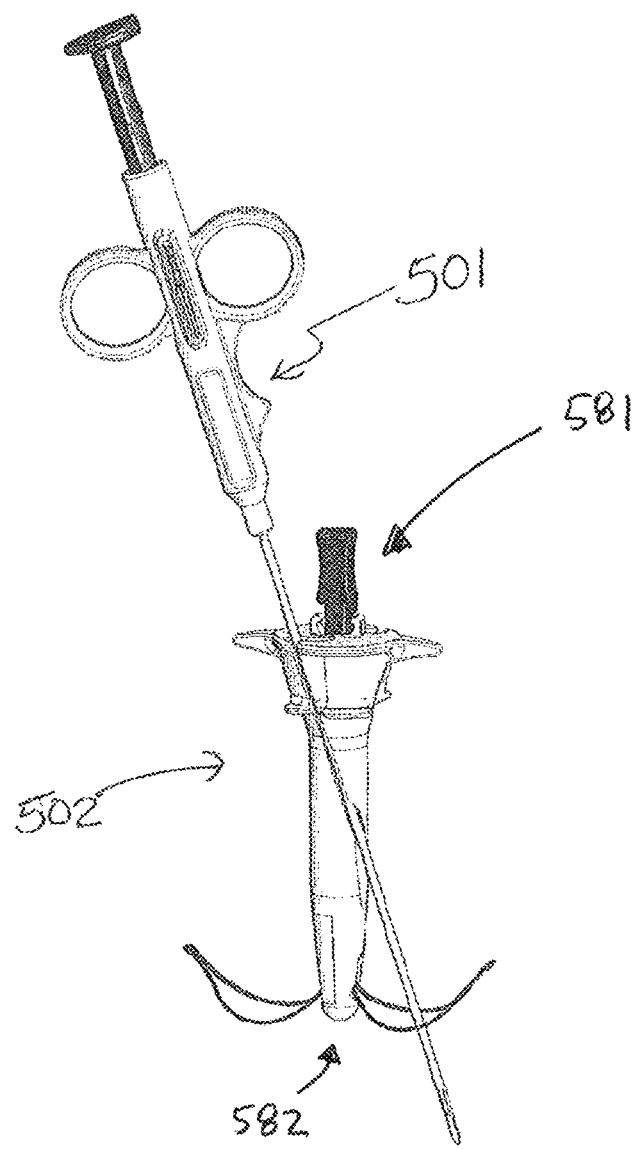
FIG. 18 illustrates an isometric view of the guide and suture engaging device.

In FIG. 18, an alternative embodiment of a guide 502 may be useful for directing a suture engaging device 501 through a body wall. The guide 502 may be particularly useful for the placement of sutures used in closing wounds or openings through body walls made in surgical procedures to access internal body cavities. Accordingly, the guide 502 preferably comprises two pathways diagonal to each other and oriented to direct a needle apparatus to both a first internal location to carry and release a first end of a suture, and a second internal location to carry and release a second end of a suture. The guide 502 comprises a proximal end 581 and a distal end 582.

Figure 20B:
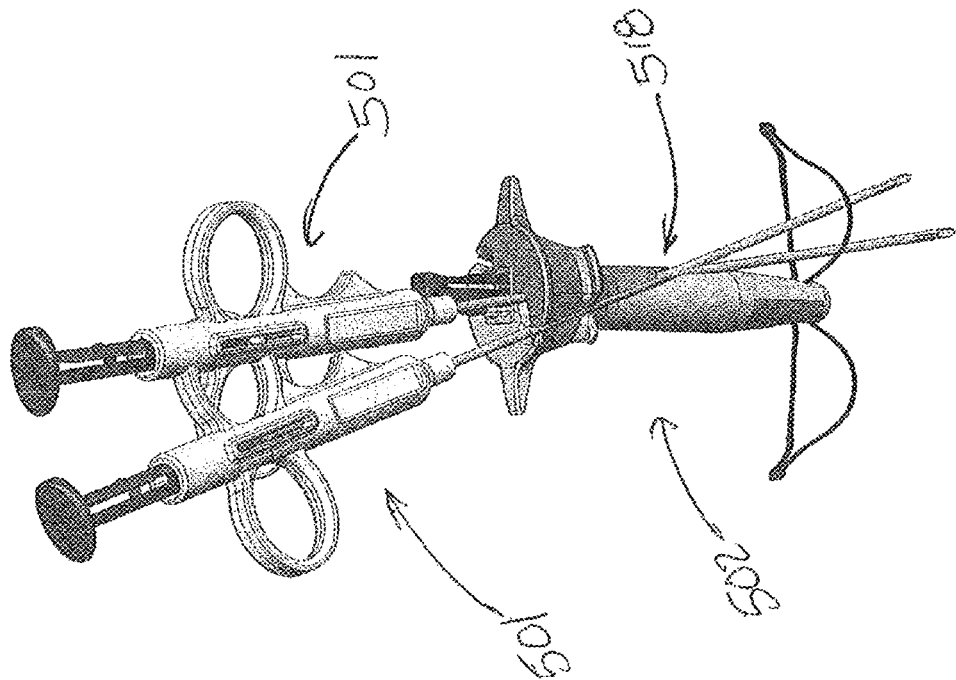
FIG. 20B illustrates an isometric view of the guide with various positions of the suture engaging device.
Figure 20A:
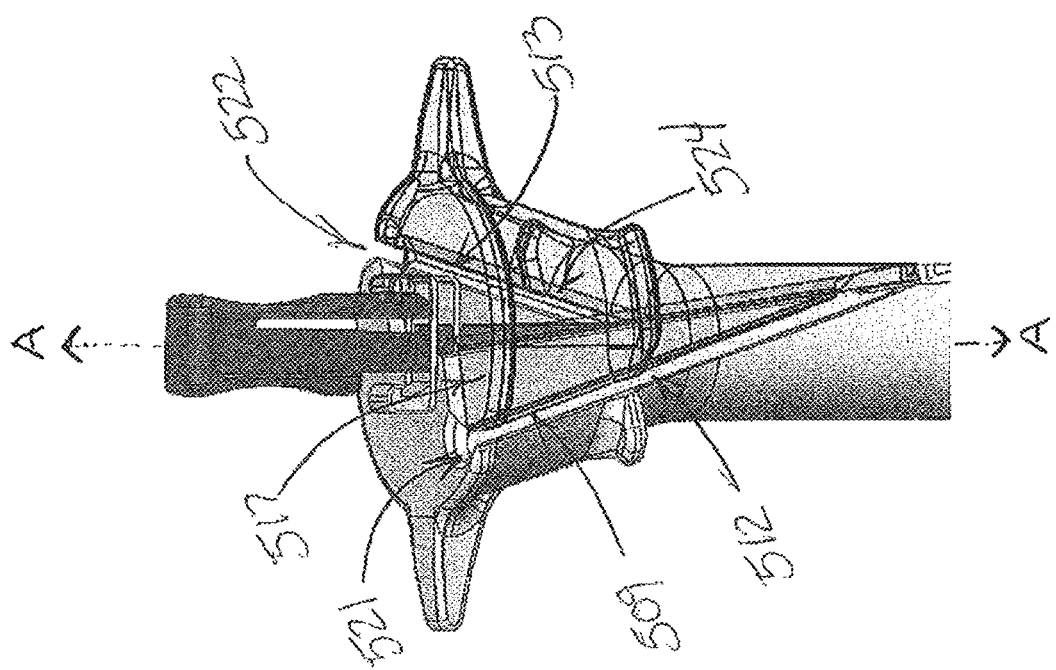
FIG. 20A illustrates a detailed view of the proximal end of the guide.

An oblique view of the preferred guide 502 is shown in FIGS. 19A-19B. The guide 502 may comprise a monolithic snare, or suture capturing mechanism, 504. The suture capturing mechanism may comprise two suture catchers 507. In a preferred embodiment, each suture catcher 507 may comprise a self-supporting snare loop 507. The guide 502 further comprises a shaft section 506, and an actuator section 505, all integrally formed. A barrel 503 comprises two channels 509, 513 as shown in FIG. 20a, and a clip 510. The barrel 503 also defines an inner lumen 520 and two or more window openings 512, 521. The barrel 503 preferably comprises two half barrel pieces 514, 515 secured to one another. The half barrel pieces 514, 515 may be identical in geometry. The barrel 503, which may be formed by securing the two half barrel pieces 514, 515 together, defines an inner lumen 520 that extends along an axis A of the guide 502, and two or more channels 509, 513 diagonal to the axis A. Each channel 509, 513 is in communication with a corresponding window opening 512, 521 located adjacent to the distal end 582. Ultrasonic welding, adhesive bonding, snap leg features, or a clip 510, or a number of other means may be used to secure the half barrel pieces 514, 515 together. The two channels 509, 513 preferably formed by the construct of the barrel half pieces 514, 515, are disposed within the barrel 503 to guide the suture passing needle 501 through the tissue to be sutured. The shaft section 506 of the monolithic snare 504 may be slidably disposed within the inner lumen 520 of the barrel 503 to provide actuation of the suture snare loops 507. The snare loops 507 may traverse within and extend laterally from the window openings 512, 521.

The tips 516 of the snare loops 507 may serve as a landmark indicator, which is used to position the guide 502 against the internal peritoneal wall. The two suture snare loops 507 serve the purpose of capturing the suture material after it has been passed through the tissue wall. The actuator section 505 of the monolithic snare 504 and tabs 508 of the barrel 503 may facilitate the ease of handling of the guide 502. Each snare loop 507 preferably comprises a pre-formed shape with memory characteristics such that the snare loop 507 consistently takes on the same shape whenever fully expanded.

Figure 22A:
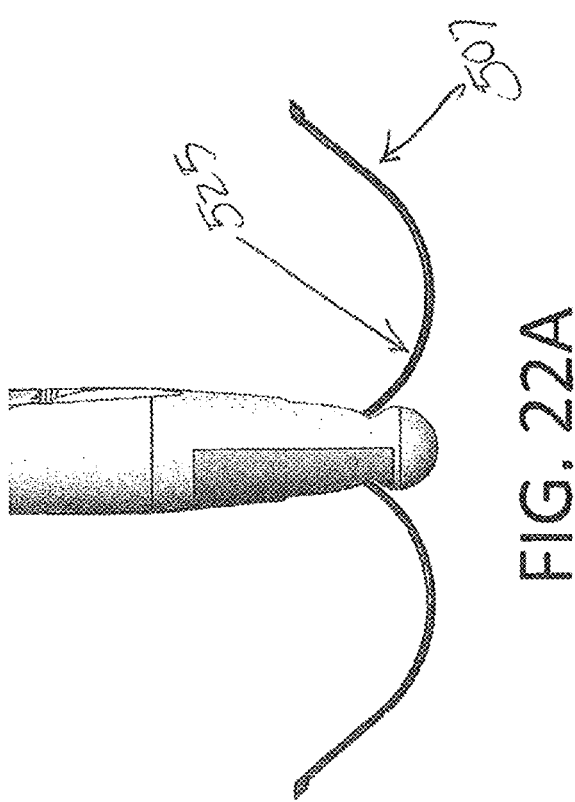
FIG. 22A illustrates a front view of the guide with snares extended.

As the actuator section 505 and shaft section 506 translate with respect to the barrel 503, the suture snare loops 507 move between two positions of radially extended shown in FIGS. 19A and 19B, and retracted shown in FIG. 21A. When each snare loop 507 is in the radially extended configuration, a pre-defined loop, ring, circle or hoop shape preferably extends laterally from the barrel 503. In the preferred embodiment, each snare loop 507 provides a corresponding C-shaped region 511 (from a side view as shown in FIG. 22A) for a suture passing needle to pass into and drop off the suture. Each region 511 is concave with respect to the proximal end 581 of the guide 502. In the preferred embodiment, each snare loop 507 is aligned with a corresponding tab 508 located directly above. Each snare loop 507 defines an opening through which the carried suture traverses. In the preferred embodiment having a pair of snare loops 507, each snare loop 507 is preferably spaced 180 degrees apart from the other and disposed distally adjacent to a corresponding channel exit point 518.

When the carried suture is released from the suture engaging device, the suture section intersecting the opening of the snare loop 507 resides loosely until the snare loop 507 is retracted. When the snare loop 507 is retracted the suture material becomes trapped between the snare loop 507 and the wall of the barrel 503 at the window opening 512 in the barrel (see, e.g., FIG. 13C). In this retracted position, the actuator section 505 is pulled away from the barrel as shown in FIG. 21A. The projecting snares loops 507 are collapsed as they are withdrawn into the window opening 512 and further into the inner lumen 520 of the barrel 503. The projecting sections of each snare loop 507 converge at the distal end to form a rigid tip 516 that points upwardly and outwardly from the barrel 503. The window opening 512 provides a recess for housing the tip 513 to allow the tip 516 from protruding outside the barrel 503 outer profile when in the retracted position, thus enabling smooth entry of the guide when being placed through the tissue track. As shown in FIG. 21b, the window opening 512 decreases in size as it extends towards the inner lumen 520. The snare tip 516 has an enlarged size or width that acts as a positive stop in combination with the narrowing window opening 512 to prevent excess proximal travel (i.e., retraction) of the monolithic snare 504 within the barrel 503.

Figure 22B:
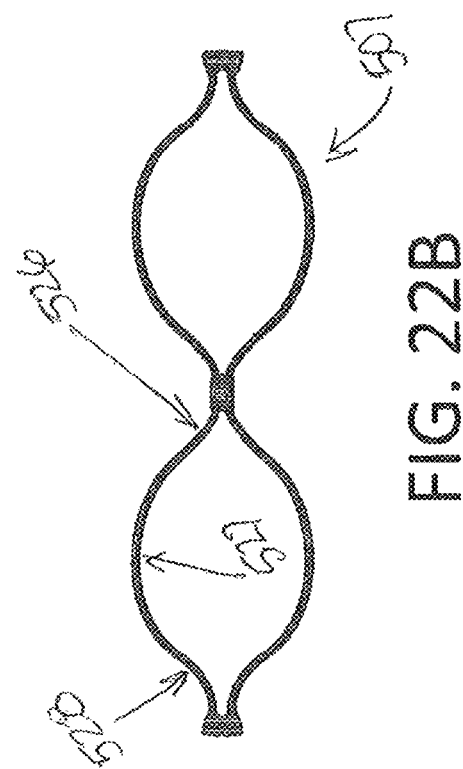
FIG. 22B illustrates a planar view of the suture catchers.

The monolithic snare 504 may be constructed from a polymer that can withstand a high degree of strain. The percent of elongation at yield may range from 3-8%. The snare loop 507 may have thin cross-sections to provide the flexibility to easily bend and conform to various geometric shapes yet stiff enough to create a self-supported snare loop that extends generally perpendicular to the long axis of the guide. The monolithic snare 504 may also extend laterally in a geometry that from a side view is a continuous radius 525 as shown in FIG. 22A. The continuous radius 525 effectively keeps the rigid tip along the "continuous radius" path as the snare loop 507 is being retracted into the barrel. The ratio of the continuous radius 525 to the cross sectional geometry of the snare loop 507 is such that the strain level of the material when retracted and constrained in the barrel 503 will not cause noticeable permanent deformation of the memorized pre-formed shape when constrained for a duration up to one hour. The same principle is true for the snare radii 526, 527, 528 as shown in the top planar view illustrated in FIG. 22B. Materials that may be used to construct the monolithic snare 504 include plastics such as nylon, polyethylene, polyester or polypropylene.

In this alternative embodiment, the guide 502 provides two different, diagonal pathways for a suture passing needle apparatus and thus comprises first and second channels 509, 513 as more clearly shown in FIG. 20A. The channels 509, 513 are directionally diagonal to the long axis A of the guide 502 at some acute angle, preferably in the range of 5-30 degrees. The angle of the channels 509, 513 controls the depth of bite into the tissue, such that a greater angle provides a greater bite of tissue. Angular spacing between entries to the channels 509, 513 are preferably equal (i.e., equiangular) depending upon the number of channels, e.g., 180 degrees apart if there are two channels, 120 degrees apart if there are three channels, etc. Therefore, channel exits are also preferably equiangular. Two separate entry points 521, 522 are provided on the channels 509, 513 for a suture passing needle to enter the guide 502, as well as two separate exit points 518, 523. Each channel 509, 513, has a corresponding slot 512, 524, or opening that allows for a strand of suture to be removed from the channel. This may be necessary to complete the suture loop in the tissue. As shown in FIGS. 20A-B, the proximal section of each channel 509, 513, may have a wider mouth including a tapered section 517 that enables angulation of the suture passing needle 501, such that a lesser angle allows a lesser bite of tissue.

Figure 23:
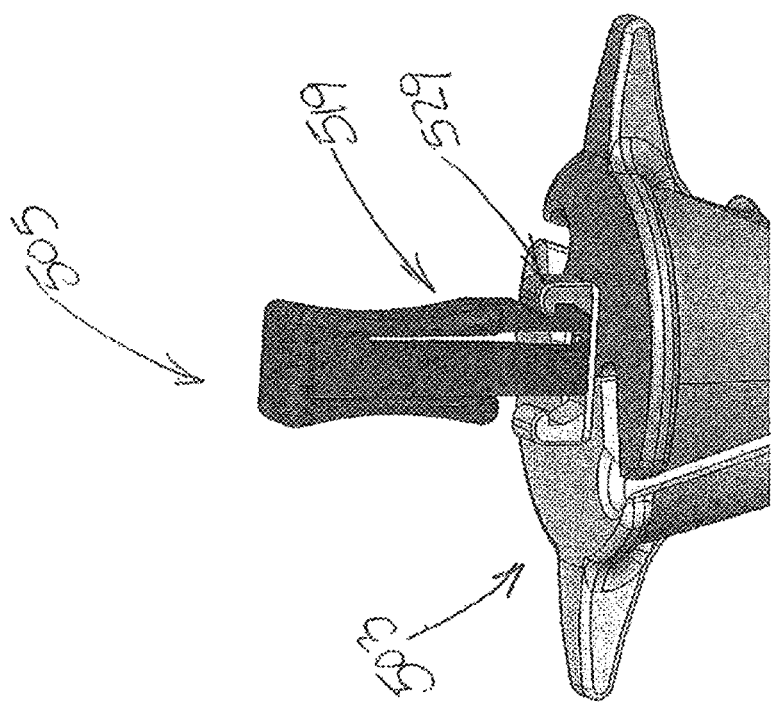
FIG. 23 illustrates a detailed view of the proximal end of the guide.

The actuation section 505 of the monolithic snare 504 may have a locking leg 519 that snap fits into a latch 529 in the barrel 503 as shown in FIG. 23. The locking leg 519 can be depressed to flex from the "locked" position to enable movement of the monolithic snare 504. The actuation section 505 may also include a variety of other connectors to facilitate a releasable locking connection between the monolithic snare 504 and the barrel 503.

Figure 24:
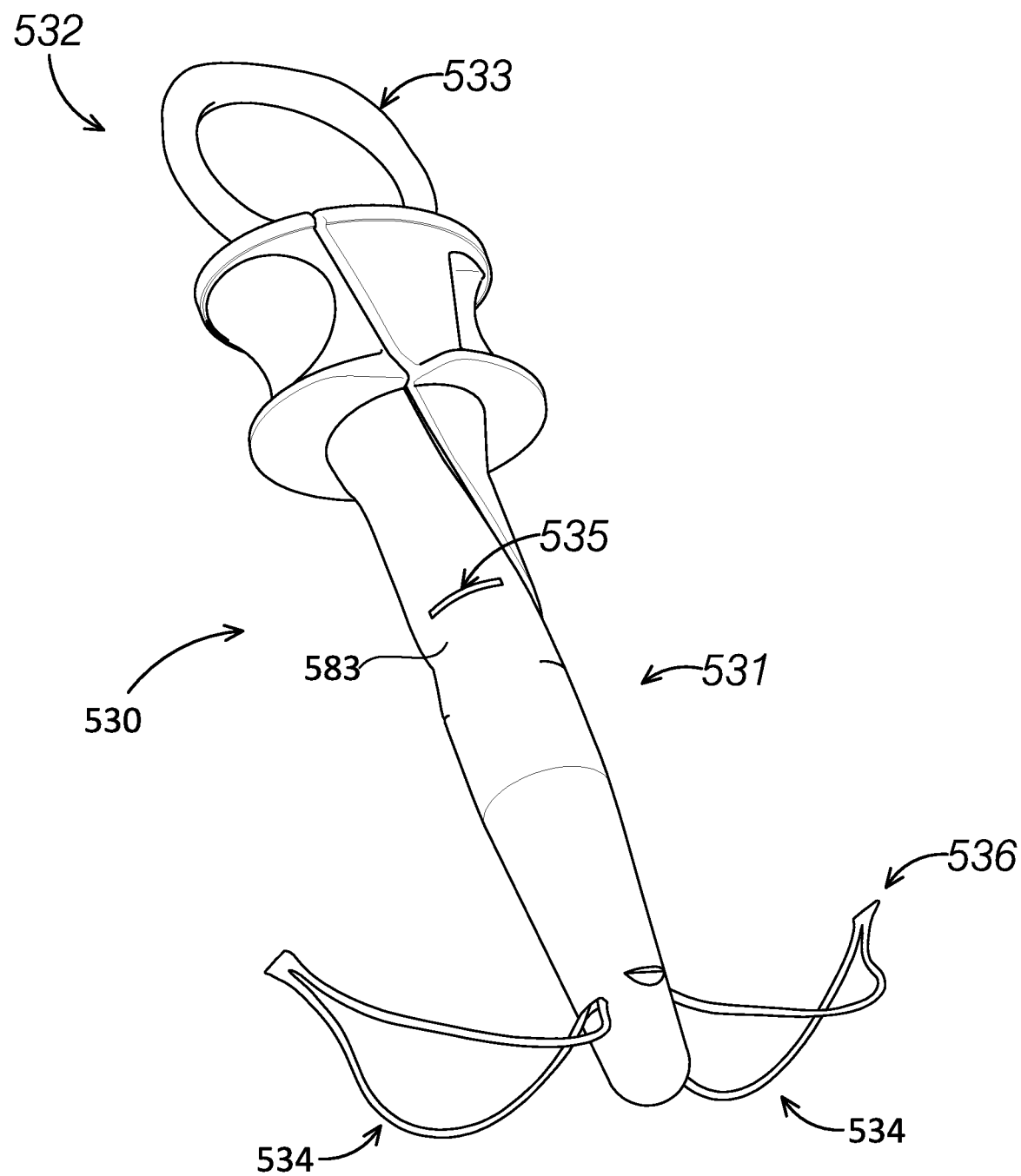
FIG. 24 illustrates an isometric view of the guide and suture engaging device.

In another embodiment shown in FIG. 24, the guide 530 comprises a barrel 531 with indicia and a monolithic snare 532 with a ring-shaped actuation section 533 for easy manipulation of the monolithic snare 532. The guide 530 includes two indicators to facilitate deployment; 1) a line mark 535 on an outer barrel surface 583, and 2) a lateral tip 536 of each snare loops 534. The two indicators can be employed in a method to accommodate proper positioning of the guide 530 in various abdominal wall thicknesses to achieve predictable suture placement in the tissue.

Figure 25B:
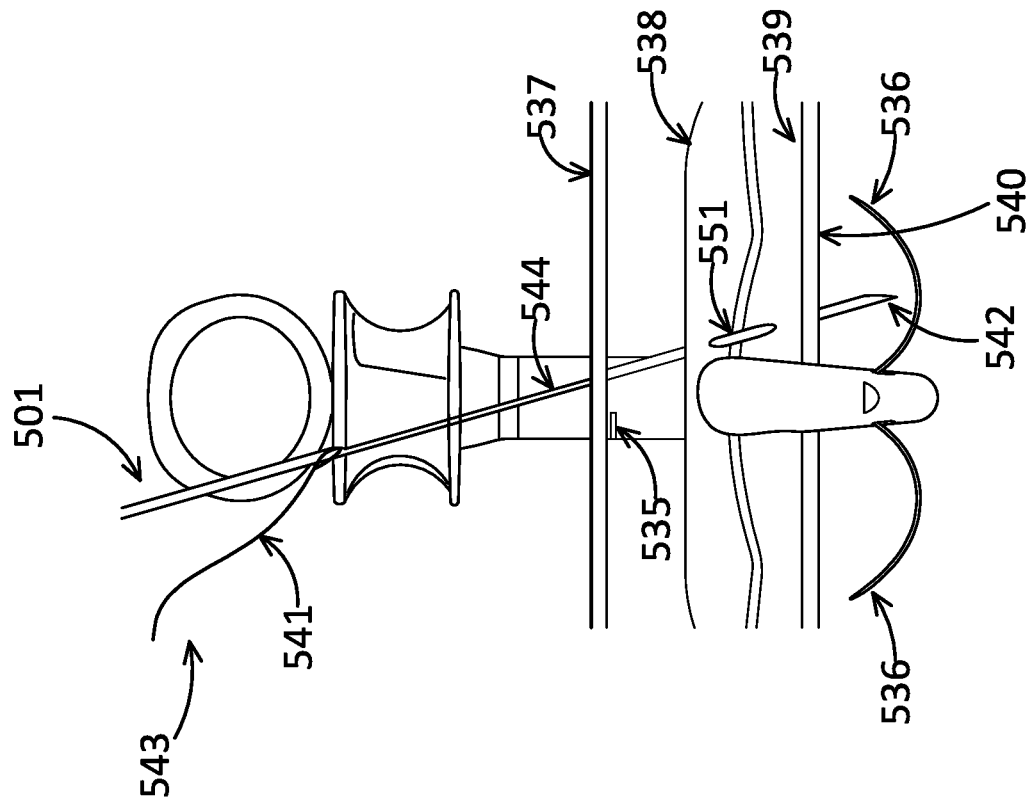
FIG. 25B illustrates detail view of the guide and needle placed in the wound.
Figure 25A:
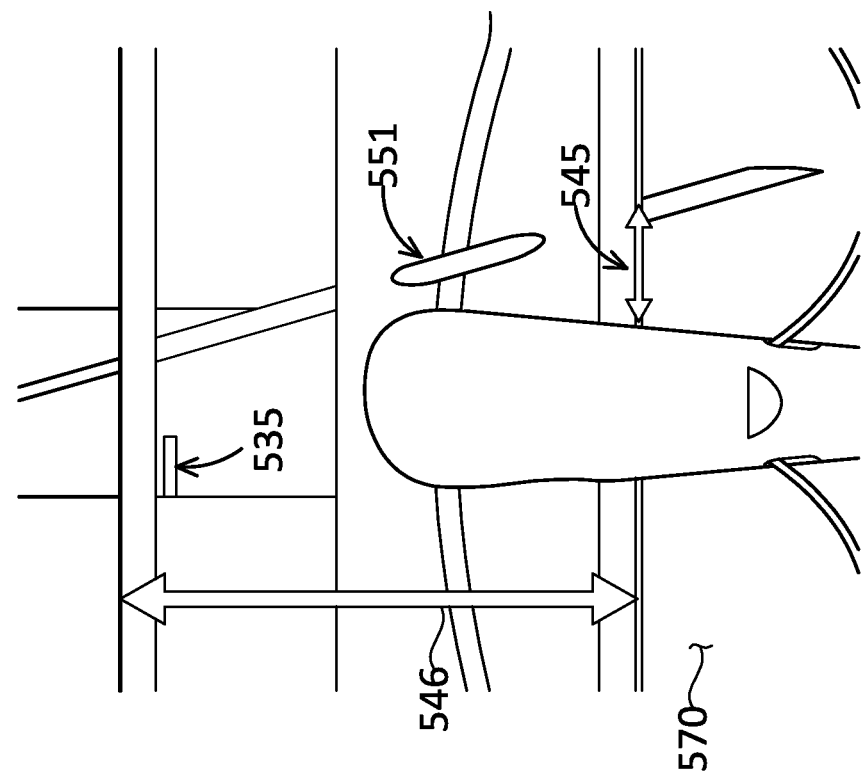
FIG. 25A illustrates front view of the guide and needle placed in the wound.

In the case of a laparoscopic surgery involving use of a trocar, the guide 530 may be placed through the tissue layers of the open trocar wound site as shown in FIGS. 25A and 25B to properly position the guide 530 within the body cavity for receiving suture carried by one or more suture engaging devices. This tissue track in the abdominal wall may include skin 537, adipose tissue 538, muscle and fascia 539 and the peritoneum 540. Prior to insertion of the guide 530 through the tissue track, the actuator section 533 may be pulled away from the barrel 530 in a proximal direction, moving the snare loops 534 into the fully retracted position to achieve the most slender profile. Once the distal end of the guide 530 is appropriately placed posterior to the peritoneal layer 540, the actuator section 533 may be pushed toward the barrel 531, extending the suture snare loops 534 to inhibit the guide 530 from exiting the body cavity. The guide 530 may then be retracted, or translated in a proximal direction away from the body cavity, until the lateral tips 536 are resting against the inner peritoneal wall 540 to position the extended snare loops 534 for receiving suture carried by the suture engaging device and to align the channels with the appropriate layers of tissue to be sutured, as shown in FIG. 25a. For patients with a relatively greater abdominal wall thickness, proximally translating the guide 530 until the expanded snare loops abut the inner peritoneal wall 540 will concurrently position both channel exits beneath the skin surface 537.

Once the guide 530 is positioned with the peritoneal wall 540 and inhibited from exiting the body cavity by the extended suture snare loops 534, the suture engaging device 501, with a first free end section 542 of suture 542 engaged, may be inserted through a first channel 544 while carrying the first section 542 of suture 541, as shown in FIG. 25A. Once the needle 551 exits the channel 544 it passes through various layers of tissue 539, 540, and enters the body cavity 570. As it enters the body cavity 570, the needle 551 passes through the first snare loop 534. The needle 551 may release the strand of suture 541 and be removed from the body leaving the suture section 542 loosely inside the expanded first snare loop 534. Thus, the suture section 542 is carried into the body cavity to a point where the suture section 542 intersects and traverses the generally planar opening defined by the expanded first snare loop 534.

The second free end section of suture 541 may then be engaged by the same suture engaging device 501 or a second engaging device, and inserted through the opposing second channel to place the second end suture section 543. Once the needle 551 exits the opposing second channel it passes through various layers of tissue 539, 540 and enters the body cavity 570. As it enters the body cavity 570, the needle 551 passes through the opposing second snare loop 534. The needle 551 may release the second strand of suture 541 and be removed from the body leaving the suture sections 542, 543 within the boundaries of the respective snare loops 534.

Moving the actuator section 533 away from the barrel retracts the snare loops 534 so as to capture the suture sections 542, 543. With both suture sections 542, 543 captured, the guide 530 is retracted from the tissue track, carrying the suture sections 542, 543. With the guide 530 and suture sections 542, 543 exposed outside the body cavity, the actuator section 533 can be pushed toward the barrel 531 extending the suture snare loops 534, and thus releasing the suture sections 542, 543. A knot can then be tied in the suture sections 542, 543 and secured to provide closure of the wound.

FIG. 25B shows the placement of the needle 501 piercing through the tissue. The distance 545 from the puncture location of the needle 501 through the peritoneum 540 to the closest edge, or perimeter, of the defect, which coincides with the sidewall of the barrel, is desirable to be nominally 8 mm. With the guide 530 positioned perpendicular to the skin surface and the lateral tips 536 resting against the inner peritoneal wall 540, the channels 544 are aligned to guide the needle 551 through the desirable amount of tissue to be sutured. However, for this method, the abdominal wall thickness 546 must be at an adequate thickness to assure the needle 551 will exit the channel 544 below the outer skin surface, or simply skin, 537 surrounding the body cavity. It is undesirable to have the suture 541 through the skin 537.

Figure 26:
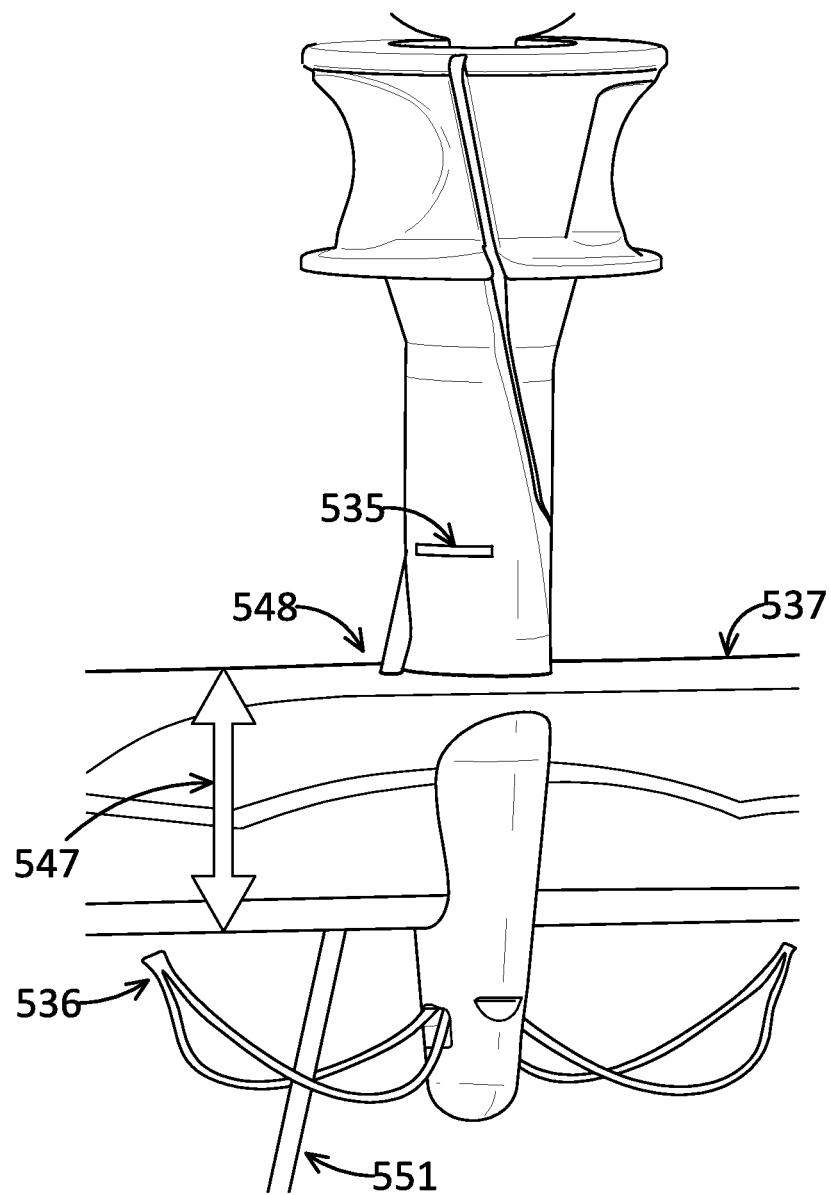
FIG. 26 illustrates front view of the guide and needle placed in the wound with the needle piercing the skin.
Figure 27B:
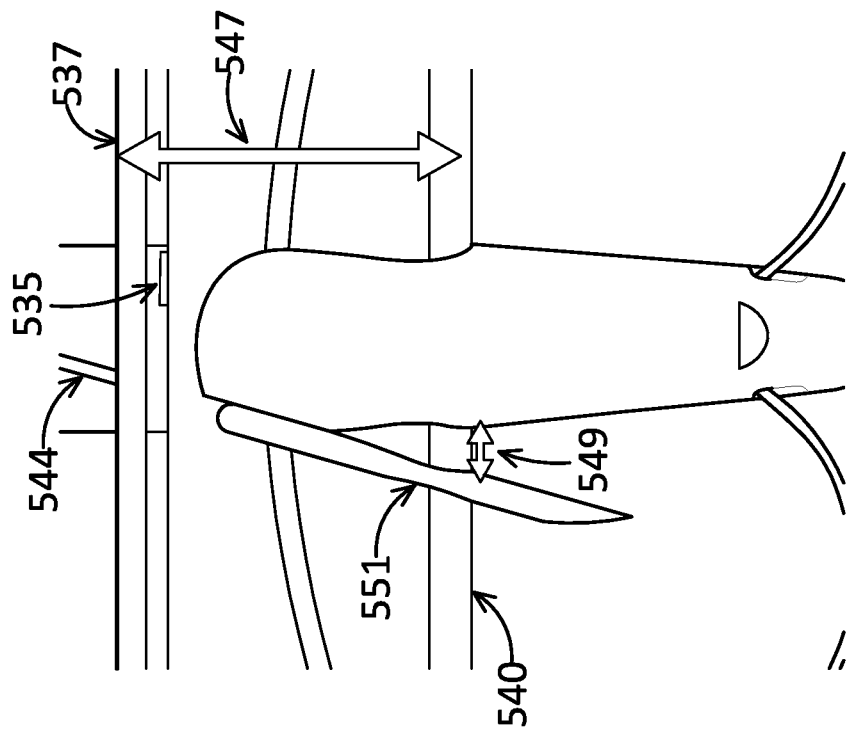
FIG. 27B illustrates detail view of the guide and needle placed deeper in the wound.
Figure 27A:
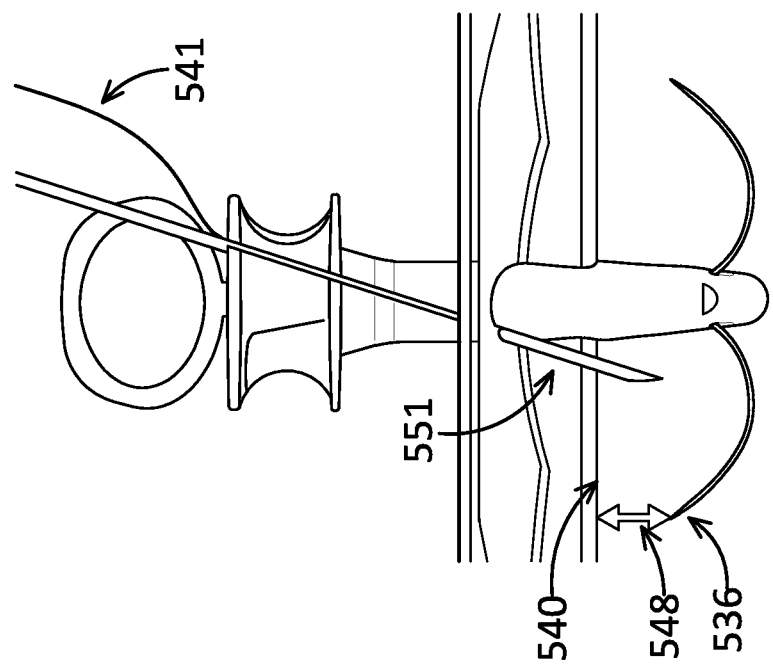
FIG. 27A illustrates front view of the guide and needle placed deeper in the wound.

FIG. 26 shows an abdominal wall thickness 547, where for the above described method of positioning the lateral tips 536 resting against the peritoneal wall 540 with the guide perpendicular to the skin surface, the thickness is not adequate. The needle is shown with a puncture 548 through the skin 537 because the channel exits are positioned above or outside the skin 537. The guide 530 needs to be inserted further into the wound for the needle 551 to avoid piercing the skin 537—namely, for the needle 551 to exit the channel exits of the guide 530 subcutaneously. An indicator in the form of a line mark 535 is provided on the outer surface of the barrel 531 as a reference. When the line mark 535 is positioned below the skin surface 537, the exit of each of the first channel 544 (shown) and second channel (not shown) will be below the outer skin surface 537 such that the needle 551 will not pierce through the skin 537. FIG. 27A shows the guide 530 inserted further in the wound, where the line mark 535 is below the skin surface 537 and thus no longer visible, such that both channel exits are positioned beneath the outer skin surface 537. This results in the lateral tips 536 being a significant distance 548 away from the peritoneum 540, thereby properly positioning the guide 530 within the cavity. FIG. 27B shows the placement of the needle 501 piercing through the tissue. The relatively shorter distance 545 from the puncture location of the needle 501 through the peritoneum 549 to the edge of the defect, which coincides with the sidewall of the barrel, may not be desirable in such thinner abdominal walls.

Figure 32:
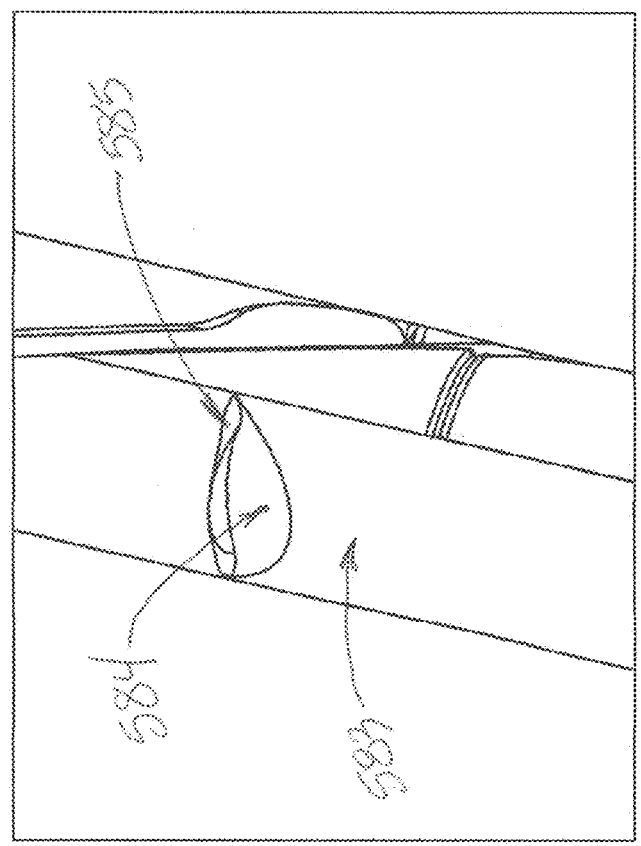
FIG. 32 illustrates a detail view of the recess feature.
Figure 31:
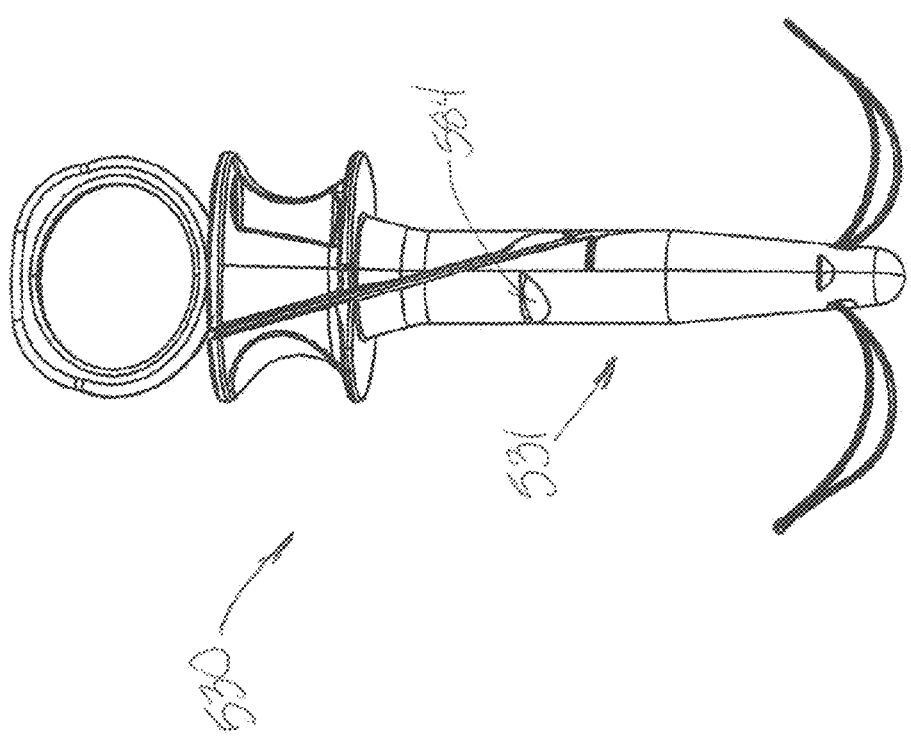
FIG. 31 illustrates isometric view of the guide with a recess feature.

An alternative indicator could be a recess or protrusion along the outer guide surface to provide a tactile feedback when the guide is translated to a position where the recess or protrusion engages the skin. FIG. 31 shows a preferred embodiment of the guide 530 with a proper depth indicator 584 comprising a recess 584. The recess 584 may be formed partially about the circumference of the barrel surface 583. Furthermore, the edge of the recess may have a radius 585 at one or both ends of the edge, as shown in FIG. 32. The radius 585 would facilitate the penetration of the barrel 531 past the skin surface with a twisting motion while applying translational force. The tactile feedback of the recess 584 abutting the skin informs the user the guide is positioned such that both channel exits are positioned beneath the outer skin surface 537. An indicator feature, such as the extended lateral tips 536 of the snare loops, may then be utilized to determine the guide position relative to the peritoneum 540, An alternative feature could be a mark on the barrel body at a level equivalent to the lateral tips of the snare. If greater guide depth is desired, the guide may be twisted while applying a translation force to penetrate the guide beyond the skin surface.

Figure 29:
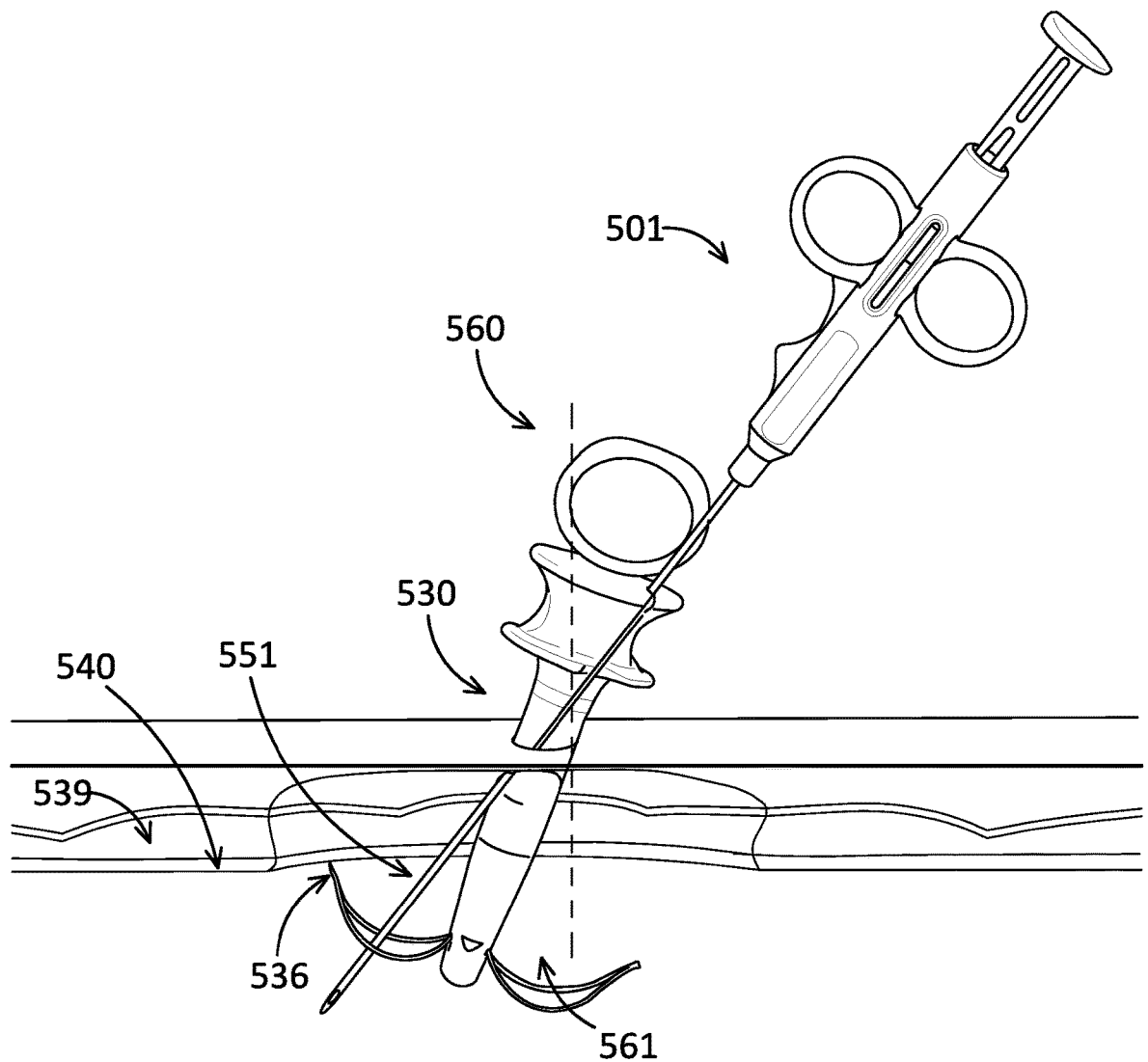
FIG. 29 illustrates isometric view of the guide and suture engaging device in the wound where the guide is tilted.

An alternative method can be used to achieve a desirable placement of the needle 551 and suture 541 through the tissue. FIG. 28A shows the guide 530 positioned in a relatively thinner abdominal wall thickness 547 as described above. FIG. 28B shows the line mark 535 below the skin 537. FIG. 28c shows the lateral tip 536 a vertical distance 548 from the peritoneum 540. Prior to the placing the needle 551 though the tissue 539, 540, the lateral tip 536 may be used as a landmark while tilting the guide 530 at an angle to the primary guide axis 560, until the first lateral tip 536 comes in close proximity to or abuts the peritoneum 540, as shown in FIG. 29. The tissue area 562 will compress, and placement of the needle 551 will encompassed a greater amount of tissue 539, 540.

With the tilted guide 530 in position, the suture engaging device 501, with a first free end section 542 of suture 542 engaged, may be inserted through a first channel 544 while carrying the section 542 of suture 541. Once the needle 551 exits the channel 544 it passes through the compressed layers of tissue 539, 540, and enters the body cavity. As it enters the body cavity, the needle 551 passes through the first snare loop 534. The needle 551 may release the strand of suture 541 and be removed from the body leaving the suture section 542 loosely inside the expanded snare loop 534. Thus, the first suture section 542 is carried into the body cavity to a point where the first suture section 542 intersects and traverses the generally planar opening defined by the expanded snare loop 534.

The guide 530 is then tilted in the opposite direction, such that the opposite second lateral tip 536 of the second snare loop 534 comes in close proximity to the peritoneum 540. With the tilted guide 530 in position, the second free end section of suture 541 may then be engaged by the suture engaging device 501, and inserted through the opposing channel to place the second end suture section 543. Once the needle 551 exits the opposing channel it passes through the compressed layers of tissue 539, 540 and enters the body cavity. As it enters the body cavity, the needle 551 passes through the opposing second snare loop 534. The needle 551 may release the strand of suture 541 and be removed from the body leaving the suture sections 542, 543 within the boundaries of the respective snare loops 534.

By tilting the guide 530 such that the lateral tip 536 of each receiving snare loop 534 comes into contact with the adjacent peritoneum 540, a greater and more desirable horizontal distance, or "bite," is achieved between each puncture location of the needle 501 through the peritoneum 540 to the closest edge of the defect coinciding with the sidewall of the barrel.

Moving the actuator section 533 away from the barrel retracts the snare loops 534 so as to capture the suture sections 542, 543. With both suture sections 542, 543 captured, the guide 530 is retracted from the tissue track, carrying the suture sections 542, 543. With the guide 530 and suture sections 542, 543 exposed outside the body cavity, the actuator section 533 can be pushed toward the barrel 531 extending the suture snare loops 534, and thus releasing the suture sections 542, 543. A knot can then be tied in the suture sections 542, 543 and secured to provide closure of the wound.

Figure 30:
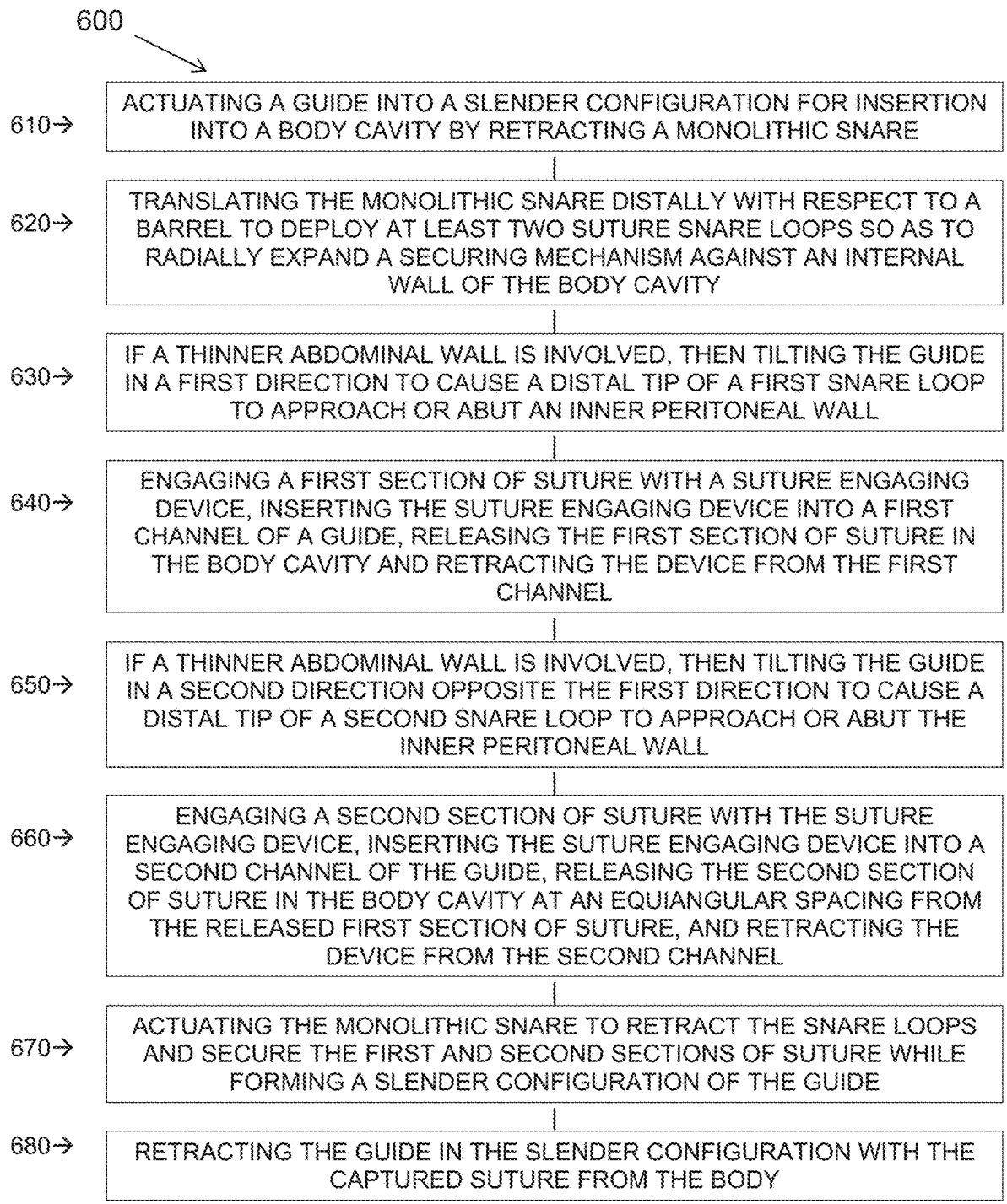
FIG. 30 illustrates an alternative method for closing a surgical wound with suture using a system comprising preferred embodiments of a suture engaging device and a guide having a monolithic snare.

FIG. 30 illustrates a preferred method 600 for closing a surgical wound using suture. Step 610 comprises actuating a guide into a slender configuration for insertion into a body cavity by retracting a monolithic snare. Step 620 comprises translating the monolithic snare distally with respect to a barrel to deploy at least two suture snare loops so as to radially expand a securing mechanism against an internal wall of the body cavity. Step 620 comprises positioning both channel exits beneath the outer surface of the skin.

If a thinner abdominal wall is involved, then optional step 630 may be employed by tilting the guide in a first direction to cause a distal tip of a first snare loop to approach or abut an inner peritoneal wall.

Step 640 comprises engaging a first section of suture with a suture engaging device, inserting the suture engaging device into a first channel of a guide, releasing the first section of suture in the body cavity and retracting the device from the first channel.

Again, if a thinner abdominal wall is involved, then optional step 650 may be employed by tilting the guide in a second direction opposite the first direction to cause a distal tip of a second snare loop to approach or abut the inner peritoneal wall.

Step 660 comprises engaging a second section of suture with the suture engaging device, inserting the suture engaging device into a second channel of the guide, releasing the second section of suture in the body cavity at an equiangular spacing from the released first section of suture, and retracting the device from the second channel. In a preferred embodiment where only two snare loops are provided, then the channel exits and associated snare loops are positioned 180 degrees from each other.

Step 670 comprises actuating the monolithic snare to retract the snare loops and secure the first and second sections of suture while forming a slender configuration of the guide. Step 670 may simply involve translating the actuation section in a proximal direction with respect to the barrel.

Step 680 comprises retracting the guide in the slender configuration with the captured suture from the body.

This method 600 may also comprise rotating the guide and repeating steps 610 through 680 to form as many stitch loops as desired.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what incorporates the essential idea of the invention.

What is claimed is:

1. A method for retrieving suture, comprising:
   inserting a guide in a slender configuration into a body cavity;
   positioning the guide in the body cavity by: deploying within the body cavity a first self-supporting suture catcher extending from a distal portion of the guide and an opposing second self-supporting suture catcher extending from the distal portion of the guide;
   directing a first section of suture configured to be attached to a distal end of a suture engaging device into the body cavity subcutaneously with a first channel in the guide;
   releasing the first section of suture, independent of the first self-supporting suture catcher, to be loosely disposed within the first self-supporting suture catcher;
   directing a second section of suture configured to be attached to a distal end of a suture engaging device into the body cavity subcutaneously with a second channel in the guide;
   releasing the second section of suture, independent of the second self-supporting suture catcher, to be loosely disposed within the second self-supporting suture catcher;
   actuating the first self-supporting suture catcher to capture the first section of suture; and
   actuating the second self-supporting suture catcher to capture the second section of suture.

2. The method of claim 1, further comprising:
   retracting the guide with the first self-supporting suture catcher and the second self-supporting suture catcher each in an expanded configuration.

3. The method of claim 2, wherein retracting the guide comprises:
   abutting a peritoneal wall of the body cavity with the first self-supporting suture catcher and the second self-supporting suture catcher each in an expanded configuration.

4. The method of claim 1, further comprising:
   positioning a first exit of the first channel and a second exit of the second channel beneath an outer skin surface surrounding the body cavity.

5. The method of claim 4, wherein positioning the first exit of the first channel and the second exit of the second channel beneath the outer skin surface comprises:
   retracting the guide from the body cavity only so far as a mark on a barrel of the guide is beneath the outer skin surface or is not visible above the outer skin surface.

6. The method of claim 1, wherein:
   the first self-supporting suture catcher comprises a first self-supporting snare loop;
   the second self-supporting suture catcher comprises a second self-supporting snare loop; and
   the deploying step comprises actuating a monolithic snare.

7. The method of claim 1, further comprising:
   retracting the guide with the captured first and second sections of suture.

8. The method of claim 7, further comprising:
   releasing the first section of suture from the first self-supporting suture catcher; and
   releasing the second section of suture from the second self-supporting suture catcher.

9. The method of claim 7, wherein retracting the guide comprises:
   translating the guide in a proximal direction away from the body cavity.

10. A method for retrieving suture, comprising:
    inserting a guide in a slender configuration into a body cavity;
    positioning the guide in the body cavity by:
        deploying within the body cavity a first self-supporting suture catcher extending from a distal portion of the guide and an opposing second self-supporting suture catcher extending from the distal portion of the guide, and
        positioning a first exit of a first channel in the guide and a second exit of a second channel in the guide beneath an outer skin surface surrounding the body cavity;
    directing a first section of suture configured to be attached to a distal end of a suture engaging device into the body cavity subcutaneously with the first channel in the guide;
    releasing the first section of suture loosely disposed within the first self-supporting suture catcher;

directing a second section of suture configured to be attached to a distal end of a suture engaging device into the body cavity subcutaneously with the second channel in the guide;

releasing the second section of suture loosely disposed within the second self-supporting suture catcher;

actuating the first self-supporting suture catcher to capture the first section of suture against a first side portion of the guide; and actuating the second self-supporting suture catcher to capture the second section of suture against a second side portion of the guide.

11. The method of claim 10, further comprising:

retracting the guide with the first self-supporting suture catcher and the second self-supporting suture catcher each in an expanded configuration.

12. The method of claim 11, wherein retracting the guide comprises:

abutting a peritoneal wall of the body cavity with the first self-supporting suture catcher and the second self-supporting suture catcher each in an expanded configuration.

13. The method of claim 11, wherein retracting the guide comprises:

translating the guide from the body cavity only so far as an indicator on a barrel of the guide is beneath the outer skin surface or is not visible above the outer skin surface.

14. The method of claim 10, further comprising:

retracting the guide with the captured first and second sections of suture.

15. The method of claim 10, wherein:

the first self-supporting suture catcher comprises a first snare loop; and the second self-supporting suture catcher comprises a second snare loop.

16. The method of claim 15, wherein the deploying step comprises actuating a monolithic snare.

17. A method for retrieving suture, comprising:

inserting a guide in a slender configuration into a body cavity;

positioning the guide in the body cavity by:

deploying within the body cavity a first self-supporting suture catcher extending from a distal portion of the guide and an opposing second self-supporting suture catcher extending from the distal portion of the guide, positioning a first exit of a first channel in the guide and a second exit of a second channel in the guide beneath an outer skin surface surrounding the body cavity, and abutting a peritoneal wall of the body cavity with the first self-supporting suture catcher and the second self-supporting suture catcher each in an expanded configuration;

directing a first section of suture configured to be attached to a distal end of a suture engaging device into the body cavity subcutaneously with the first channel in the guide;

releasing the first section of suture loosely disposed within the first self-supporting suture catcher;

directing a second section of suture configured to be attached to a distal end of a suture engaging device into the body cavity subcutaneously with the second channel in the guide;

releasing the second section of suture loosely disposed within the second self-supporting suture catcher;

actuating the first self-supporting suture catcher to capture the first section of suture;

actuating the second self-supporting suture catcher to capture the second section of suture; and retracting the guide with the captured first and second sections of suture.

18. The method of claim 17, further comprising:

retracting the guide with the first self-supporting suture catcher and the second self-supporting suture catcher each in an expanded configuration.

19. The method of claim 18, wherein retracting the guide comprises:

translating the guide from the body cavity only so far as an indicator on a barrel of the guide is beneath the outer skin surface.

20. The method of claim 17, wherein:

the first self-supporting suture catcher comprises a first self-supporting snare loop; and the second self-supporting suture catcher comprises a second self-supporting snare loop.

21. The method of claim 20, wherein the deploying step comprises actuating a monolithic snare.

* * * * *